United States Patent
Ignagni

(10) Patent No.: US 11,471,683 B2
(45) Date of Patent: Oct. 18, 2022

(54) SYSTEMS AND METHODS FOR TREATING SLEEP APNEA USING NEUROMODULATION

(71) Applicant: Synapse Biomedical, Inc., Oberlin, OH (US)

(72) Inventor: Anthony R. Ignagni, Oberlin, OH (US)

(73) Assignee: Synapse Biomedical, Inc., Oberlin, OH (US)

( * ) Notice: Subject to any disclaimer, the term of this patent is extended or adjusted under 35 U.S.C. 154(b) by 229 days.

(21) Appl. No.: 16/776,440

(22) Filed: Jan. 29, 2020

(65) Prior Publication Data

US 2020/0238084 A1 Jul. 30, 2020

Related U.S. Application Data

(60) Provisional application No. 62/798,335, filed on Jan. 29, 2019.

(51) Int. Cl.
*A61N 1/36* (2006.01)
*A61N 1/05* (2006.01)
*A61N 1/04* (2006.01)

(52) U.S. Cl.
CPC .......... *A61N 1/3611* (2013.01); *A61N 1/0452* (2013.01); *A61N 1/0556* (2013.01); *A61N 1/3601* (2013.01)

(58) Field of Classification Search
CPC .. A61N 1/3611; A61N 1/0452; A61N 1/0556; A61N 1/3601
See application file for complete search history.

(56) References Cited

U.S. PATENT DOCUMENTS

| 1,693,734 A | 12/1928 | Waggoner |
| 2,532,788 A | 12/1950 | Sarnoff |
| 2,664,880 A | 1/1954 | Wales, Jr. |

(Continued)

FOREIGN PATENT DOCUMENTS

| EP | 996482 A1 | 5/2000 |
| EP | 873155 B1 | 6/2003 |

(Continued)

OTHER PUBLICATIONS

Akers et al.; Tissue response to chronically stimulated implanted epimysial and intramuscular electrodes; IEEE Transactions on Rehabilitation Engineering; 5(2); pp. 207-220; Jun. 1997.

(Continued)

*Primary Examiner* — Unsu Jung
*Assistant Examiner* — Philip C Edwards
(74) *Attorney, Agent, or Firm* — Shay Glenn LLP

(57) ABSTRACT

Methods and systems for treating sleep apnea using electrical stimulation to a patient's upper and/or lower respiratory nerve or muscle are described. A stimulation regimen can be used to achieve upper airway patency and/or rhythmic air flow in a coordinated fashion during sleep. In some cases, diaphragm activity is monitored to determine whether sufficient upper airway patency and/or rhythmic air flow is achieved and maintained. The stimulation regimen may be adjusted based on the diaphragm activity. In some cases, the system includes modularized components so that the components can be customized to an individual's needs.

23 Claims, 11 Drawing Sheets

(56) References Cited

U.S. PATENT DOCUMENTS

| | | |
|---|---|---|
| 4,192,305 A | 3/1980 | Seberg |
| 4,699,875 A | 10/1987 | Appel |
| 4,702,260 A | 10/1987 | Wang |
| 4,773,393 A | 9/1988 | Haber et al. |
| 4,827,935 A | 5/1989 | Geddes et al. |
| 4,830,008 A | 5/1989 | Meer |
| 4,863,438 A | 9/1989 | Gauderer et al. |
| 4,989,617 A | 2/1991 | Memberg et al. |
| 5,056,519 A | 10/1991 | Vince |
| 5,074,846 A | 12/1991 | Clegg et al. |
| 5,146,918 A | 9/1992 | Kallok et al. |
| 5,314,463 A | 5/1994 | Camps et al. |
| 5,335,657 A | 8/1994 | Terry et al. |
| 5,368,035 A | 11/1994 | Hamm et al. |
| 5,429,636 A | 7/1995 | Shikhman et al. |
| 5,472,438 A | 12/1995 | Schmit et al. |
| 5,483,969 A | 1/1996 | Testerman et al. |
| 5,524,632 A | 6/1996 | Stein et al. |
| 5,527,358 A | 6/1996 | Mehmanesh et al. |
| 5,678,535 A | 10/1997 | DiMarco |
| 5,716,392 A | 2/1998 | Bourgeois et al. |
| 5,718,248 A | 2/1998 | Trumble et al. |
| 5,792,165 A | 8/1998 | Klieman et al. |
| 5,797,923 A | 8/1998 | Aiyar et al. |
| 5,800,451 A | 9/1998 | Buess et al. |
| 5,813,399 A | 9/1998 | Isaza et al. |
| 5,814,086 A | 9/1998 | Hirschberg et al. |
| 5,849,290 A | 12/1998 | Brown et al. |
| 5,851,783 A | 12/1998 | Appel et al. |
| 6,035,856 A | 3/2000 | LaFontaine et al. |
| 6,194,217 B1 | 2/2001 | Matson |
| 6,198,970 B1 | 3/2001 | Freed et al. |
| 6,210,970 B1 | 4/2001 | Matson |
| 6,245,053 B1 | 6/2001 | Benjamin |
| 6,254,425 B1 | 7/2001 | Shchervinsky et al. |
| 6,311,692 B1 | 11/2001 | Vaska et al. |
| 6,321,109 B2 | 11/2001 | Ben-Haim et al. |
| 6,360,740 B1 | 3/2002 | Ward et al. |
| 6,397,108 B1 | 5/2002 | Camps et al. |
| 6,405,732 B1 | 6/2002 | Edwards et al. |
| 6,415,183 B1 | 7/2002 | Scheiner et al. |
| 6,463,327 B1 | 10/2002 | Lurie et al. |
| 6,477,423 B1 | 11/2002 | Jenkins |
| 6,571,127 B1 | 5/2003 | Ben-Haim et al. |
| 6,645,145 B1 | 11/2003 | Dreschel et al. |
| 6,845,271 B2 | 1/2005 | Fang et al. |
| 6,918,871 B2 | 7/2005 | Schulze |
| 6,947,792 B2 | 9/2005 | Ben-Haim et al. |
| 7,006,871 B1 | 2/2006 | Darvish et al. |
| 7,044,921 B2 | 5/2006 | Asmus et al. |
| 7,071,194 B2 | 7/2006 | Teng |
| 7,107,092 B2 | 9/2006 | Goldstein et al. |
| 7,120,497 B2 | 10/2006 | Ben-Haim et al. |
| 7,155,278 B2 | 12/2006 | King et al. |
| 7,165,551 B2 | 1/2007 | Edwards et al. |
| 7,195,881 B2 | 3/2007 | Geffard |
| 7,206,636 B1 | 4/2007 | Turcott |
| 7,207,946 B2 | 4/2007 | Sirokman |
| 7,221,978 B2 | 5/2007 | Ben-Haim et al. |
| 7,225,016 B1 | 5/2007 | Koh |
| 7,329,489 B2 | 2/2008 | Kaddurah-Daouk et al. |
| 7,356,521 B2 | 4/2008 | Wang et al. |
| 7,418,298 B2 | 8/2008 | Shiroff et al. |
| 7,840,270 B2 | 11/2010 | Ignagni et al. |
| 7,962,215 B2 | 6/2011 | Ignagni et al. |
| 8,406,885 B2 | 3/2013 | Ignagni et al. |
| 8,428,726 B2 | 4/2013 | Ignagni et al. |
| 8,478,412 B2 | 7/2013 | Ignagni et al. |
| 8,676,323 B2 | 3/2014 | Ignagni et al. |
| 8,706,236 B2 | 4/2014 | Ignagni et al. |
| 9,050,005 B2 | 6/2015 | Ignagni et al. |
| 9,079,016 B2 | 7/2015 | Ignagni et al. |
| 9,138,580 B2 | 9/2015 | Ignagni et al. |
| 9,820,671 B2 | 11/2017 | Ignagni et al. |
| 2001/0025177 A1 | 9/2001 | Woloszko et al. |
| 2001/0049497 A1 | 12/2001 | Kalloo et al. |
| 2002/0103424 A1 | 8/2002 | Swoyer et al. |
| 2003/0040785 A1 | 2/2003 | Maschino et al. |
| 2003/0148404 A1 | 8/2003 | Michaelson |
| 2003/0171672 A1 | 9/2003 | Varghese et al. |
| 2003/0175832 A1 | 9/2003 | Marton et al. |
| 2003/0195600 A1 | 10/2003 | Tronnes et al. |
| 2004/0003813 A1 | 1/2004 | Banner et al. |
| 2004/0044377 A1 | 3/2004 | Larsson |
| 2004/0064069 A1 | 4/2004 | Reynolds et al. |
| 2004/0122360 A1 | 6/2004 | Waldhauser et al. |
| 2004/0127954 A1 | 7/2004 | McDonald |
| 2004/0167437 A1 | 8/2004 | Sharrow et al. |
| 2004/0167442 A1 | 8/2004 | Shireman et al. |
| 2004/0167443 A1 | 8/2004 | Shireman et al. |
| 2004/0172090 A1 | 9/2004 | Janzig et al. |
| 2004/0177388 A1 | 9/2004 | Botas et al. |
| 2004/0254572 A1 | 12/2004 | Mcintyre et al. |
| 2004/0260198 A1 | 12/2004 | Rothberg et al. |
| 2004/0260245 A1 | 12/2004 | Clem et al. |
| 2004/0260246 A1 | 12/2004 | Desmond |
| 2004/0260337 A1 | 12/2004 | Freed |
| 2005/0033394 A1 | 2/2005 | Seifert et al. |
| 2005/0042589 A1 | 2/2005 | Hatlestad et al. |
| 2005/0049523 A1 | 3/2005 | Crank |
| 2005/0054950 A1 | 3/2005 | Parins |
| 2005/0054951 A1 | 3/2005 | Parins |
| 2005/0054952 A1 | 3/2005 | Eskuri et al. |
| 2005/0080463 A1 | 4/2005 | Stahmann et al. |
| 2005/0085734 A1 | 4/2005 | Tehrani |
| 2005/0085865 A1 | 4/2005 | Tehrani |
| 2005/0085866 A1 | 4/2005 | Tehrani |
| 2005/0085867 A1 | 4/2005 | Tehrani et al. |
| 2005/0085868 A1 | 4/2005 | Tehrani et al. |
| 2005/0085869 A1 | 4/2005 | Tehrani et al. |
| 2005/0107781 A1 | 5/2005 | Ostrovsky et al. |
| 2005/0107812 A1 | 5/2005 | Starksen et al. |
| 2005/0107860 A1 | 5/2005 | Ignagni et al. |
| 2005/0109340 A1 | 5/2005 | Tehrani |
| 2005/0113710 A1 | 5/2005 | Stahmann et al. |
| 2005/0115561 A1 | 6/2005 | Stahmann et al. |
| 2005/0124917 A1 | 6/2005 | Skujins et al. |
| 2005/0137501 A1 | 6/2005 | Euteneuer et al. |
| 2005/0148026 A1 | 7/2005 | Bowser et al. |
| 2005/0148818 A1 | 7/2005 | Mesallum |
| 2005/0165457 A1 | 7/2005 | Benser et al. |
| 2005/0209653 A1 | 9/2005 | Herbert et al. |
| 2005/0240241 A1 | 10/2005 | Yun et al. |
| 2005/0277945 A1 | 12/2005 | Saadat et al. |
| 2006/0030894 A1 | 2/2006 | Tehrani |
| 2006/0035849 A1 | 2/2006 | Spiegelman et al. |
| 2006/0036294 A1 | 2/2006 | Tehrani |
| 2006/0041022 A1 | 2/2006 | Pasinetti |
| 2006/0068452 A1 | 3/2006 | Goldknopf et al. |
| 2006/0088862 A1 | 4/2006 | Lee |
| 2006/0115854 A1 | 6/2006 | Goldknopf et al. |
| 2006/0115855 A1 | 6/2006 | Goldknopf et al. |
| 2006/0115856 A1 | 6/2006 | Goldknopf et al. |
| 2006/0115867 A1 | 6/2006 | Goldknopf et al. |
| 2006/0121619 A1 | 6/2006 | Bowser |
| 2006/0122662 A1 | 6/2006 | Tehrani et al. |
| 2006/0130161 A1 | 6/2006 | Genain |
| 2006/0130833 A1 | 6/2006 | Younes |
| 2006/0142815 A1 | 6/2006 | Tehrani et al. |
| 2006/0149316 A1 | 7/2006 | DeVries et al. |
| 2006/0149334 A1 | 7/2006 | Tehrani et al. |
| 2006/0155222 A1 | 7/2006 | Sherman et al. |
| 2006/0155341 A1 | 7/2006 | Tehrani et al. |
| 2006/0160087 A1 | 7/2006 | McGrath et al. |
| 2006/0167523 A1 | 7/2006 | Tehrani et al. |
| 2006/0200664 A1 | 9/2006 | Wilk |
| 2006/0224209 A1 | 10/2006 | Meyer |
| 2006/0237023 A1 | 10/2006 | Cox et al. |
| 2006/0247729 A1 | 11/2006 | Tehrani et al. |
| 2006/0258667 A1 | 11/2006 | Teng |
| 2006/0281809 A1 | 12/2006 | Miller et al. |
| 2006/0282131 A1 | 12/2006 | Caparso et al. |
| 2006/0286167 A1 | 12/2006 | Staunton et al. |
| 2006/0287679 A1 | 12/2006 | Stone |

(56) References Cited

U.S. PATENT DOCUMENTS

| | | | |
|---|---|---|---|
| 2007/0016172 A1 | 1/2007 | Charukhchian | |
| 2007/0017809 A1 | 1/2007 | Goldknopf et al. | |
| 2007/0021421 A1 | 1/2007 | Hampton | |
| 2007/0021500 A1 | 1/2007 | Twyman et al. | |
| 2007/0021795 A1 | 1/2007 | Tehrani | |
| 2007/0038127 A1 | 2/2007 | Goldstein et al. | |
| 2007/0054852 A1 | 3/2007 | Lin et al. | |
| 2007/0072943 A1 | 3/2007 | Miller et al. | |
| 2007/0078099 A1 | 4/2007 | McLaurin | |
| 2007/0087000 A1 | 4/2007 | Walsh et al. | |
| 2007/0087314 A1 | 4/2007 | Gomo | |
| 2007/0096812 A1 | 5/2007 | Feinstein et al. | |
| 2007/0117772 A1 | 5/2007 | Bennett et al. | |
| 2007/0118183 A1 | 5/2007 | Gelfand et al. | |
| 2007/0122813 A1 | 5/2007 | Salomon et al. | |
| 2007/0150023 A1 | 6/2007 | Ignagni et al. | |
| 2007/0156006 A1 | 6/2007 | Libbus et al. | |
| 2007/0172820 A1 | 7/2007 | Kaddurah-Daouk et al. | |
| 2007/0191908 A1 | 8/2007 | Jacob et al. | |
| 2007/0196780 A1 | 8/2007 | Ware et al. | |
| 2007/0197932 A1 | 8/2007 | Feke et al. | |
| 2007/0202515 A1 | 8/2007 | Hadlock et al. | |
| 2007/0202537 A1 | 8/2007 | Lingappa et al. | |
| 2007/0221224 A1 | 9/2007 | Pittman et al. | |
| 2007/0225261 A1 | 9/2007 | Miller et al. | |
| 2007/0240718 A1 | 10/2007 | Daly | |
| 2007/0250162 A1 | 10/2007 | Royalty | |
| 2007/0274992 A1 | 11/2007 | Michalovich et al. | |
| 2007/0282388 A1 | 12/2007 | Sandyk | |
| 2007/0292403 A1 | 12/2007 | Nivaggioli | |
| 2007/0292410 A1 | 12/2007 | Cashman et al. | |
| 2007/0298998 A1 | 12/2007 | Paige et al. | |
| 2008/0003208 A1 | 1/2008 | Nivaggioli | |
| 2008/0027476 A1 | 1/2008 | Piskun | |
| 2008/0051824 A1 | 2/2008 | Gertner | |
| 2008/0097153 A1 | 4/2008 | Ignagni et al. | |
| 2008/0121231 A1 | 5/2008 | Sinderby et al. | |
| 2008/0167695 A1* | 7/2008 | Tehrani | A61N 1/3601 607/42 |
| 2008/0208282 A1* | 8/2008 | Gelfand | A61N 1/3601 607/42 |
| 2009/0182402 A1 | 7/2009 | Glukhovsky | |
| 2010/0016749 A1* | 1/2010 | Atsma | A61B 5/4818 600/529 |
| 2010/0125310 A1 | 5/2010 | Wilson et al. | |
| 2012/0029362 A1* | 2/2012 | Patangay | A61N 1/0548 600/484 |
| 2012/0290044 A1 | 11/2012 | Logan | |
| 2013/0231735 A1 | 9/2013 | Deem et al. | |
| 2015/0283383 A1* | 10/2015 | Ternes | A61N 1/36139 607/20 |
| 2018/0036033 A1 | 2/2018 | Ignagni et al. | |
| 2018/0104481 A1 | 4/2018 | Boggs et al. | |

FOREIGN PATENT DOCUMENTS

| | | |
|---|---|---|
| EP | 1634617 A1 | 3/2006 |
| EP | 1653863 A2 | 5/2006 |
| EP | 1658020 A1 | 5/2006 |
| EP | 1660177 A1 | 5/2006 |
| EP | 1663370 A2 | 6/2006 |
| EP | 1667757 A2 | 6/2006 |
| EP | 1670611 A2 | 6/2006 |
| EP | 1684655 A2 | 8/2006 |
| EP | 1393773 B1 | 10/2006 |
| EP | 1306104 B1 | 1/2007 |
| EP | 1205202 B1 | 6/2007 |
| WO | WO 86/00234 A1 | 1/1986 |
| WO | WO 2005/039691 A1 | 5/2005 |
| WO | WO 2005/044079 A2 | 5/2005 |
| WO | WO 2006/062710 A1 | 6/2006 |
| WO | WO 2006/079152 A1 | 8/2006 |
| WO | WO 2006/083675 A2 | 8/2006 |
| WO | WO 2006/088696 A2 | 8/2006 |
| WO | WO 2006/121447 A2 | 11/2006 |
| WO | WO 2006/124023 A1 | 11/2006 |
| WO | WO 2006/131150 A1 | 12/2006 |
| WO | WO 2006/138069 A1 | 12/2006 |
| WO | WO 2007/035804 A2 | 3/2007 |
| WO | WO 2007/053230 A2 | 5/2007 |
| WO | WO 2007/058780 A2 | 5/2007 |
| WO | WO 2007/058938 A2 | 5/2007 |
| WO | WO 2007/061902 A2 | 5/2007 |
| WO | WO 2007/082384 A1 | 7/2007 |
| WO | WO2007/085822 A1 | 8/2007 |
| WO | WO 2007/109443 A2 | 9/2007 |
| WO | WO 2007/128002 A2 | 11/2007 |

OTHER PUBLICATIONS

Ayas et al; Prevention of human diaphragm atrophy with short periods of electrical stimulation; Am J Respir Crit Care Med; vol. 159; pp. 2018-2020; Jun. 1, 1999.

Bhadra et al.; Extraction force and tissue change during removal of a tined intramuscular electrode from rat gastroonemius, Annals of Biomedical Engineering; vol. 34; No. 6; pp. 1042-1050; Jun. 2006.

Boon et al.; Ultrasound-guided needle EMG of the diaphragm: technique description and case report; Muscle Nerve; 38(6); pp. 1623-1626; Dec. 1, 2008.

Boon et al.; Two-dimensional ultrasound imaging of the diaphragm: quantitative values in normal subjects; Muscle and Nerve; 47(6); pp. 884-889; Jun. 1, 2013.

Caldwell et al.; A percutaneous wire electrode for chronic research use; IEEE Transactions on Biomedical Engineering; 22(5); pp. 429-432; Sep. 1975.

D'Honneur et al.; Comparison of the effects of mivacurium on the diaphragm and geniohyoid muscles; British Journal of Anesthesia; 77(6); pp. 716-719; Dec. 1996.

DeCarvalho et al.; Motor neuron disease presenting with respiratory failure; Journal of the Neurological Sciences; voi. 139; No. Suppl.; pp. 117-122; Aug. 31, 1996.

De Carvalho et al.; Medical technology assessment: Electrodiagnosis in motor neuron diseases and amyotrophic lateral sclerosis; Neurophysiol. Clin.; 31 (5); pp. 341-348; Oct. 2001.

DiMarco et al.; Phrenic nerve pacing in a tetraplegic patient via intramuscular diaphragm electrodes; American Journal of Respiratory and Critical Care Medicine; vol. 166 (12 Pt 1); pp. 1604-1606; Dec. 15, 2002.

DiMarco A. F.; Restoration of respiratory muscle function following spinal cord injury—Review of electrical and magnetic stimulation techniques; Respiratory Physiology & Neurobiology; 147: 273-287; Jul. 28, 2005.

Johnson et al.; Visualization of the diaphragm muscle with ultrasound improves diagnostic accuracy of phrenic nerve conduction studies; Muscle and Nerve; 49(5): pp. 669-675; May 1, 2014.

Kalloo et al.; Flexible transgastric peritoneoscopy: a novel approach to diagnosis and therapeutic intervention in the peritoneal cavity; Gastrointestinal Endoscopy: vol. 60: No. 1: pp. 114-117; Jul. 31, 2004.

Knutson et al.; Electrode fracture rates and occurrences of infection and granuloma associated with percutaneous intramuscular electrodes in upper-limb functional electrical stimulation applications; Journal of Rehabilitation Research and Development; vol. 39; No. 6; pp. 671-684, Nov./Dec. 2002.

Majumder et al ; Overcoming respiratory morbidity of abdominal wall reconstruction: will temporary diaphragm pacing be the solution?; Presentation at the Americas Hernia Society's 17th annual Conference, Washington, DC; 2 pages, Mar. 30-Apr. 2, 2016.

Marsolais et al.; Implantation techniques and experience with percutaneous intramuscular electrodes in the lower extremities; J. Rehabil. Res. Dev.; 23(3); pp. 1-8; Jul. 1, 1986.

McGee et al.; A reliable method for monitoring intraabdominal pressure during natural orifice translumenal endoscopic surgery; Surg Endosc.; 21(4): pp. 672-676; Apr. 2007.

Nochomovitz et al.; Conditioning of the diaphragm with phrenic nerve stimulation after prolonged disuse, American Review of Respiratory Disease; vol. 130; No. 4; 325-329; Oct. 1984.

(56) References Cited

OTHER PUBLICATIONS

Nochomovitz et al.; Diaphragm activation with intramuscular stimulation in dogs; American Review of Respiratory Disease; vol. 127; No. 3; 685-687; Mar. 1983.

Onders et al.; Early results of laparoscopic motor point diaphragm pacing in amyotrophic lateral sclerosis; Amyotrophic Lateral Sclerosis (Abstracts from the 16th Intl. Symp. ALS/MND; vol. 6, supp. 1; ISSN1743-4475; pp. 142-143; Dec. 2005.

Onders et al.; Mapping the phrenic nerve motor point: the key to a successful laparoscopic diaphragm pacing system in the first human series; Surgery; vol. 136; No. 4; 819-26; Oct. 2004.

Onders, Raymond P.; The Utility of Flexible Endoscopy During Advanced Laparoscopy; Seminars in Laparoscopic Surgery; vol. 10, No. 1; pp. 43-48; Mar. 2003.

Onders et al.: Prospective FDA feasibility trial of laparoscopically placed temporary diaphragm pacing electrodes: a new reversible therapy to treat respiratory failure; Presentation at the Scientific Session of the Society of American Gastrointestinal and endoscopic Surgeons (SAGES); Boston,Mass.; 11 pages; (year of pub. sufficiently earlier than effective US filing date and any foreign priority date) 2016.

Peterson et al.; Long-term intramuscular electrical activation of the phrenic nerve: Safety and reliability; IEEE; vol. 41; No. 12; pp. 1115-1126; Dec. 1994.

Peterson et al.; Electrical activation of respiratory muscles by methods other than phrenic nerve cuff electrodes; Pacing and Clinical Electrophysiology; vol. 12; No. 5; pp. 854-878; May 1989.

Peterson et al.; Intramuscular electrical activation of the phrenic nerve; IEEE Transactions on Biomedical Engineering; vol. BME-33; No. 3; 342-351; Mar. 1986.

Polkey et al.; Influence of acute lung volume change on contractile properties of human diaphragm; Journal of Applied Physiology; vol. 85, No. 4; pp. 1322-1328; Oct. 1998.

Sarnoff et al.; Electrophrenic respiration; Science; vol. 108; 482; Oct. 29, 1948.

Schmit, et al.; Laparoscopic placement of electrodes for diaphragm pacing using stimulation to locate the phrenic nerve motor points; IEEE Trans on Rehab Engineer; vol. 6; No. 4; 382-390; Dec. 1998.

Shalgholi et al.; Diaphragm depth in normal subjects; Muscle Nerve; 49(5); pp. 666-668; May 1, 2014.

Stewart et al.; Electromyography of respiratory muscles in amyotrophic lateral sclerosis; Journal of the Neurological Sciences; vol. 191; No. 1-2; Oct. 15, 2001; pp. 67-73.

Wang et al.; Case report: Artificial pleural effusion in percutaneous microwave ablation of hepatic tumors near the diaphragm under the guidance of ultrasound; International Journal of Clinical and Experimental Medicine; 8(9); pp. 16765-16771; Sep. 15, 2015.

Yu et al.; Percutaneous intramuscular neuromuscular electric stimulation for the treatment of shoulder subluxation and pain in patients with chronic hemiplegia: A pilot study; Archives of physical medicine and rehabilitation; 82(1); pp. 20-25; Jan. 31, 2001.

Zifko et al.; Central and peripheral respiratory electrophysiological studies in myotonic dystrophy; Brain; vol. 119(6); pp. 1911-1922; Dec. 1, 1996.

Ignagni et al.; U.S. Appl. No. 17/710,896 entitled "Systems and methods for electrode placement in deep muscles and nerves using ultrasound guidance," filed Mar. 31, 2022.

\* cited by examiner

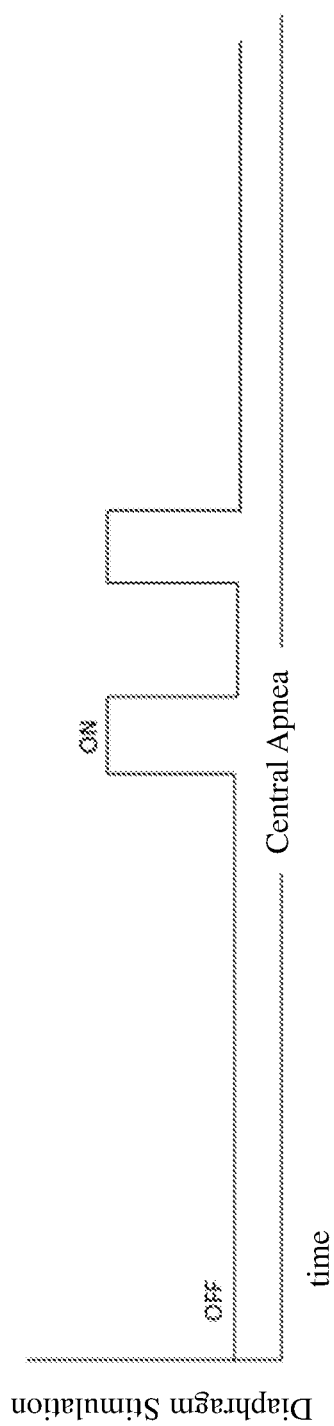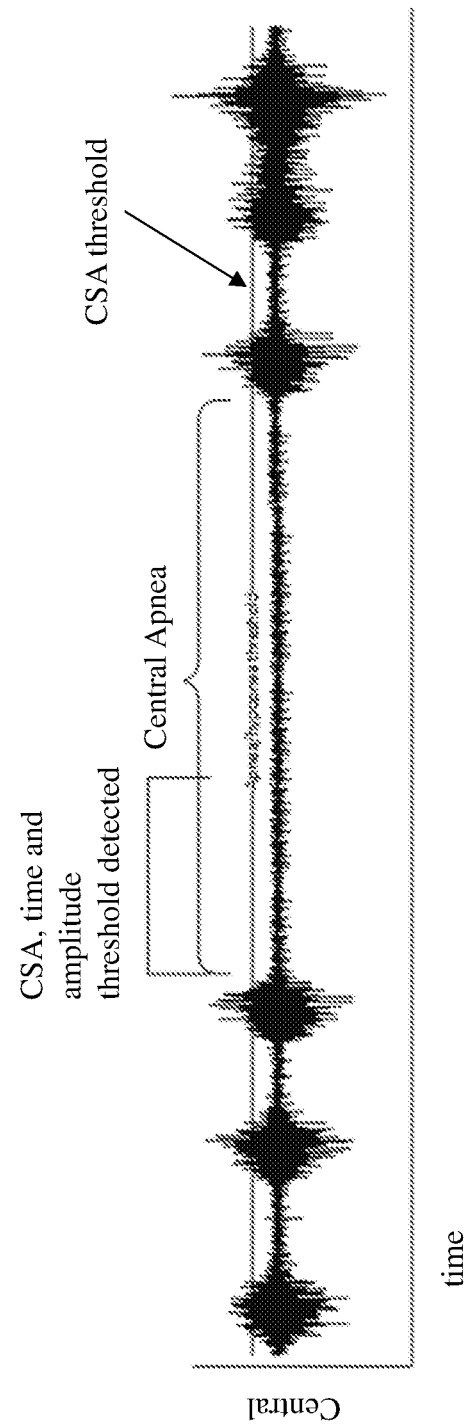
FIG. 7A
FIG. 7B

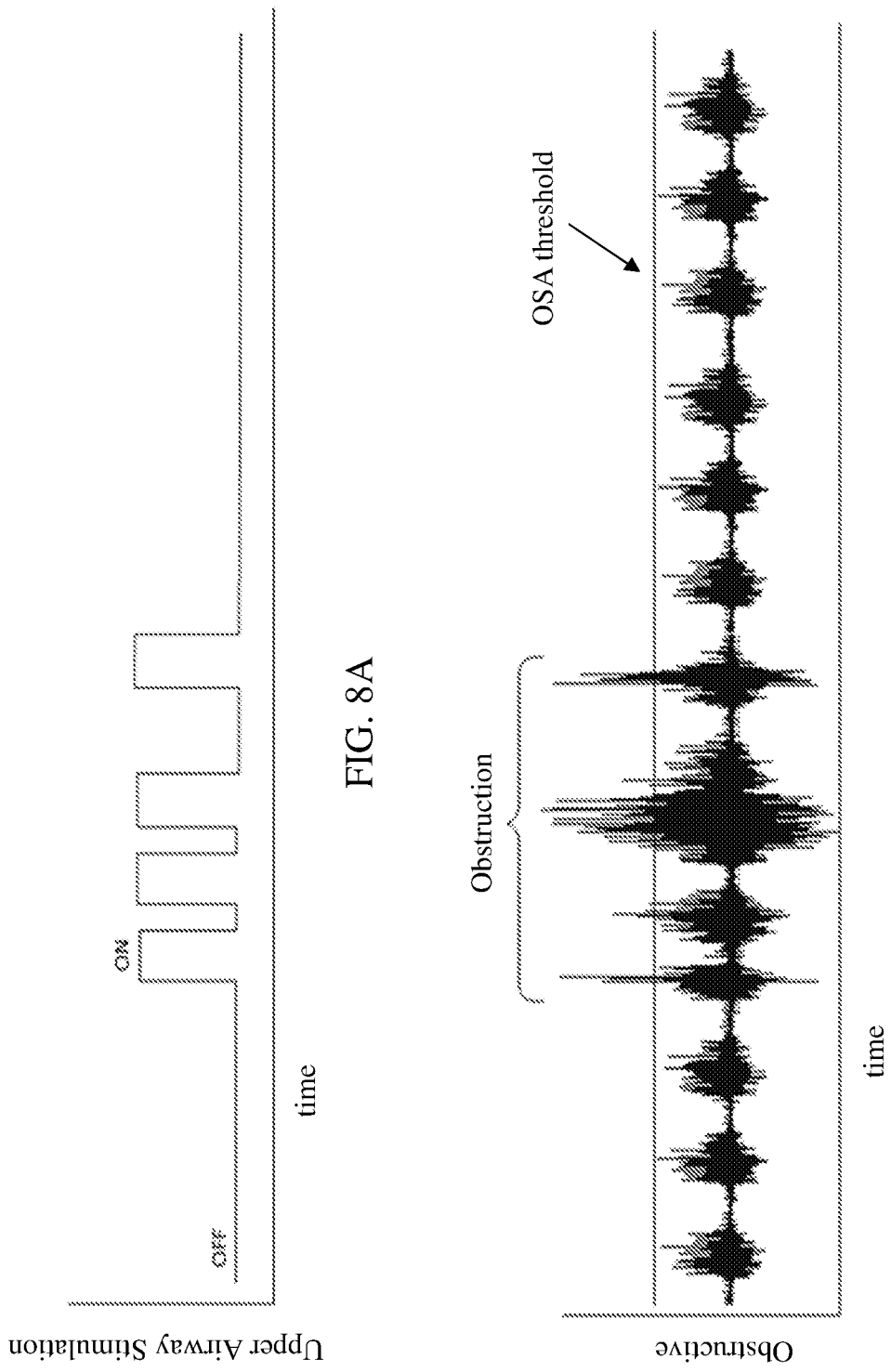

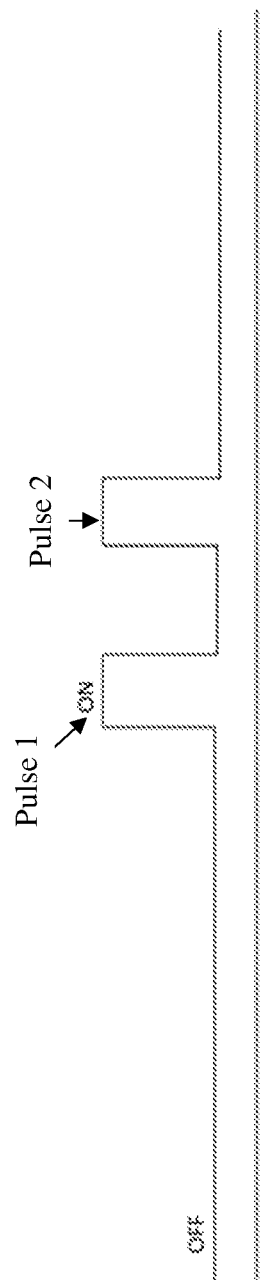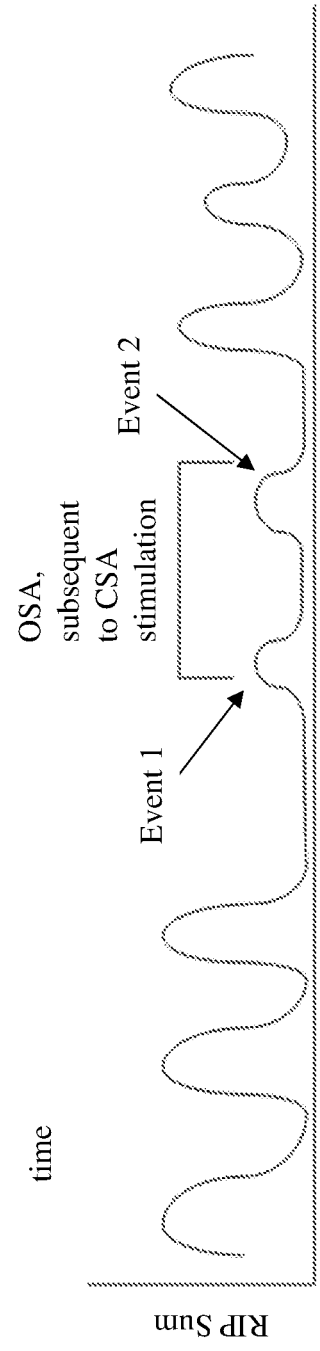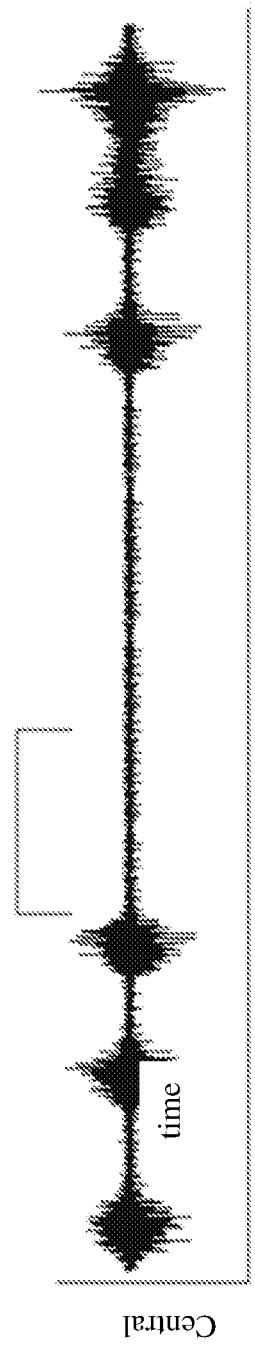
FIG. 9A
FIG. 9B
FIG. 9C

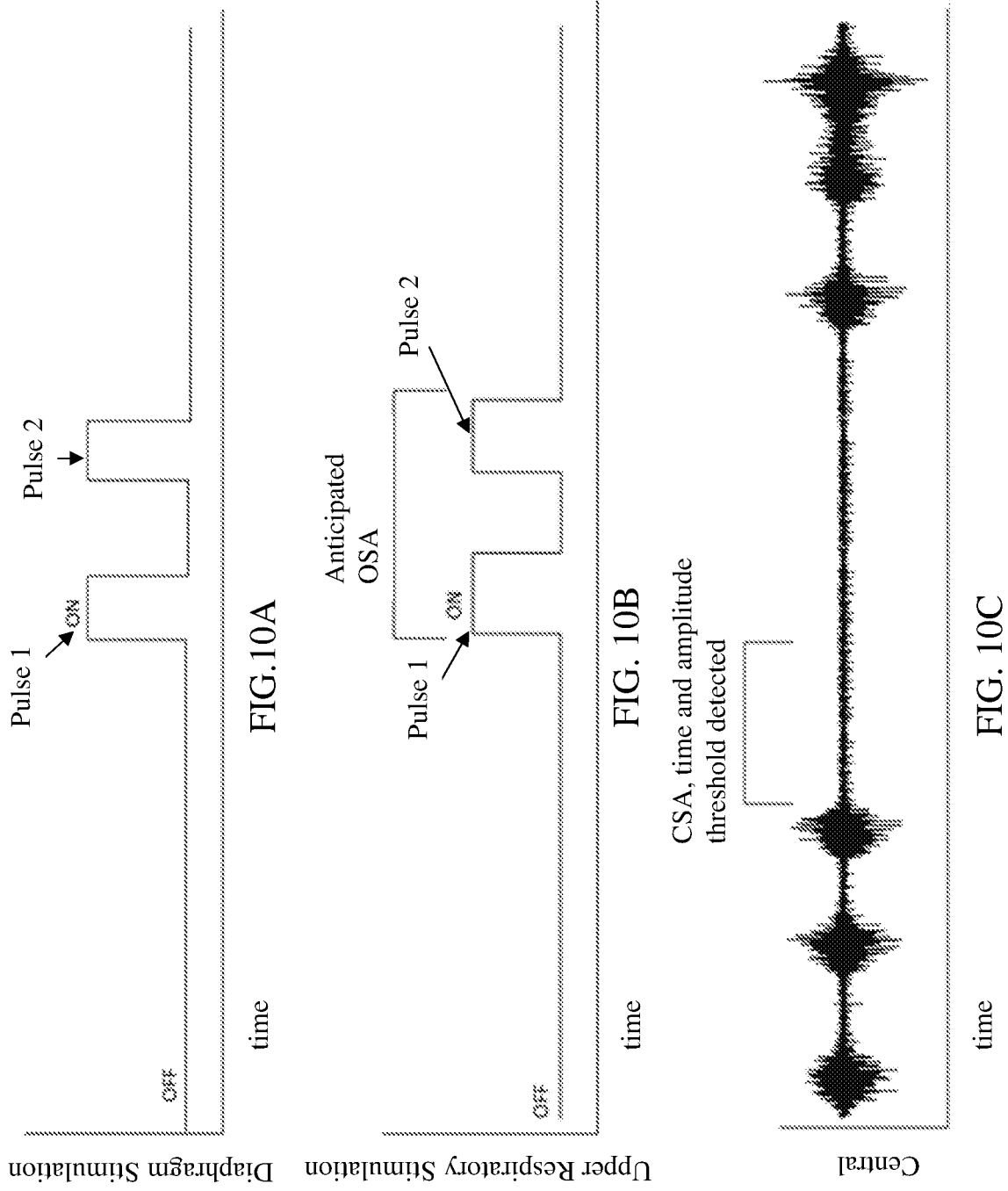

SYSTEMS AND METHODS FOR TREATING SLEEP APNEA USING NEUROMODULATION

CROSS REFERENCE TO RELATED APPLICATIONS

This patent application claims priority to U.S. Provisional Patent Application No. 62/798,335, filed on Jan. 29, 2019, which is herein incorporated by reference in its entirety.

INCORPORATION BY REFERENCE

All publications and patent applications mentioned in this specification are herein incorporated by reference to the same extent as if each individual publication or patent application was specifically and individually indicated to be incorporated by reference.

BACKGROUND

Sleep apnea is a complex disease that results in the inability of a patient to effectively fill their lungs with air. The source of the inability may be singular, mixed or vary over time. An obstruction of the upper airway may block the airflow into the lungs, formally referred to as obstructive sleep apnea. A loss or lapse of signal from the brain may cause a cessation of respiration, formally referred to as central sleep apnea. These two types of apnea may also combine to create what is referred to as mixed apnea. Additionally, the respiration may take on the presentation of lapses of respiration followed by couplets of respiration, known as Cheyne-Stokes respiration.

Methods of treating sleep apnea include positive pressure techniques such as continuous positive airway pressure (CPAP) and automatic positive airway pressure (APAP) techniques. However, a significant percentage of patients do not tolerate positive pressure interventions well. Other techniques involve stimulation of the hypoglossal nerve to push the tongue slightly forward, thereby removing the obstruction and opening the airway. Hypoglossal nerve stimulation techniques may treat the obstruction but are not conventionally able to affect central apneas or Cheyne Stokes respiration. Further methods include diaphragm pacing, which involves application of electrical impulses to cause the diaphragm to contract rhythmically, thereby inducing rhythmic inspiration. Diaphragm pacing methods however are conventionally limited to treating central sleep apnea and not airway obstructions. Thus, neither of these techniques may adequately address mixed type sleep apnea. Furthermore, the contribution of central and obstructive types of sleep apnea may vary over time, making the sleep apnea complex and difficult to treat over time. What are needed therefore are improved methods and devices for resolving sleep apnea, including mixed and complex types of sleep apnea.

SUMMARY

The methods, devices and systems described herein can be used to treat various types of sleep apnea, including obstructive, central and mixed type. The methods can include electrically stimulating the upper respiratory tract, the lower respiratory tract, or both. The systems described herein can include features for implementing a therapeutic stimulation regimen on a trial basis (e.g., using a percutaneous system) or a more permanent basis (e.g., using an implantable system). In some cases, the systems include modularized components so that the components can be easily replaced and customized to an individual's needs.

According to some embodiments, a method of treating sleep apnea includes: (a) repeatedly stimulating one or both of a phrenic nerve and the diaphragm in accordance with a rhythmic air flow; and (b) stimulating an upper respiratory nerve to maintain an upper airway patency during (a). The stimulating in (b) may be varied based on a pattern of stimulations in (a). The stimulating in (b) may include stimulating or increasing stimulus intensity of the upper respiratory nerve during periods when one or both of the phrenic nerve and the diaphragm is stimulated. The stimulating in (b) may include maintaining a stimulus intensity of the upper respiratory nerve during (a). In some cases, the method further includes monitoring diaphragm activity and modulating one or both of (a) and (b) based on the diaphragm activity. Monitoring diaphragm activity can include sensing muscle activity using one or more electrodes placed at one or more locations of the diaphragm. The one or more locations can include an intramuscular location of the diaphragm or on the phrenic nerve trunk. The one or more locations can include an inferior or a superior aspect location of the diaphragm. Modulating one or both of (a) and (b) can include performing one or more of the following: performing (a) or increasing stimulus intensity in (a) when the diaphragm activity is below a lower threshold; and performing (b) or increasing stimulus intensity in (b) when the diaphragm activity is above an upper threshold. Increasing stimulus intensity can include increasing an electrical current delivered to the upper respiratory nerve, the phrenic nerve or the diaphragm.

According to a further embodiment, a method of treating sleep apnea includes: stimulating an upper respiratory nerve with a therapeutic regimen of electrical stimulations to create upper airway patency; monitoring diaphragm activity to determine whether the therapeutic regimen maintains the upper airway patency; and adjusting the therapeutic regimen based on the monitoring. Adjusting the therapeutic regimen can include increasing a stimulus intensity or frequency for stimulating the upper respiratory nerve when the diaphragm activity is above an upper threshold. Monitoring diaphragm activity can include monitoring diaphragm electromyographic (EMG) data. The upper respiratory nerve can include one or both of the hypoglossal nerve or the recurrent laryngeal nerve. The therapeutic regimen may be adjusted over a period of a single sleep period. The therapeutic regimen may be adjusted over a period of a multiple sleep periods.

According to a further embodiment, a system for treating sleep apnea includes: one or more controllers; one or more stimulating electrodes operably coupled to the one or more controllers and arranged to stimulate an upper respiratory nerve; one or more sensing electrodes arranged to sense activity of the diaphragm; and a processor arranged to cause the one or more controllers to apply a therapeutic regimen of electrical stimulations for achieving upper airway patency to the upper respiratory nerve via the one or more stimulating electrodes, wherein the processor is further arranged to capture the sensed activity of the diaphragm and cause the one or more controllers to modify the therapeutic regimen of electrical stimulations based on the sensed activity. The one or more controllers can be part of a primary implantable module that is operationally coupled to one or more secondary implantable modules, wherein the one or more secondary implantable modules are operationally coupled to the one or more stimulating electrodes and one or more sensing electrodes. The one or more stimulating electrodes can be associated with a first secondary implantable module, wherein the one or more sensing electrodes are associated with a second secondary implantable module. The system can further include a third secondary implantable module associated with one or more simulating electrodes for stimulating the upper respiratory tract. The processor and the one or more controllers can be part of an electronic stimulator external to the body and configured to communicate with the one or more stimulating electrodes and one or more sensing electrodes via percutaneous connectors. The one or more controllers can be part of an electronic stimulator that is implantable within the body and configured to communicate with the one or more stimulating electrodes and one or more sensing electrodes via wire connections. The one or more stimulating and sensing electrodes can include a monopolar or bipolar electrode. The one or more stimulating electrodes or the one or more sensing electrodes can include an intramuscular electrode. The one or more stimulating electrodes or the one or more sensing electrodes can include a cuff electrode. The one or more stimulating electrodes may be on the hypoglossal nerve or the recurrent laryngeal nerve, and the one or more sensing electrodes may be in or on the diaphragm.

According to an additional embodiment, a method of treating sleep apnea includes: (a) stimulating a patient's diaphragm with a therapeutic regimen of electrical stimulations in accordance with a rhythmic air flow; and (b) monitoring air flow and/or blood oxygenation of the patient during (a) to determine the presence of one or more obstructive airflow events. The method can further include (c) determining the presence of the one or more obstructive airflow events; and (d) stimulating the patient's upper airway with a second therapeutic regimen of electrical stimulations to reduce the occurrence or severity of the obstructive airflow events. Stimulating the patient's upper airway can include implementing a pulse of electrical stimulation for an anticipated obstructive airflow event. Monitoring the air flow and/or the blood oxygenation of the patient can include sensing a breathing pattern and/or oxygen desaturation of the patient.

According to another embodiment, a method of treating a patient's sleep apnea symptoms includes: screening the patient for the ability to overcome central apnea symptoms using a percutaneous trial neuromodulation system, wherein screening the patient comprises determining whether the patient has underlying obstructive apnea symptoms; and configuring an implantable neuromodulation system to apply a stimulation regimen based on results from the screening using the percutaneous trial neuromodulation system. Determining whether the patient has underlying obstructive apnea symptoms can include applying a central apnea stimulation regimen to treat the central apnea symptoms while monitoring the patient for the presence of obstructive apnea symptoms. Screening the patient can include determining that the patient is able to tolerate a stimulation regimen that reduces the central apnea symptoms and/or the obstructive apnea symptoms. The method can further include implanting the implantable neuromodulation system in the patient. Screening the patient can include placing temporary electrodes on the diaphragm of the patient. The temporary electrodes can be used to sense diaphragm activity that indicate the presence of central apnea symptoms, and to stimulate the diaphragm to treat the central apnea symptoms. The sensed diaphragm activity may be logged as data in the percutaneous trial neuromodulation system, wherein the logged data is accessible for evaluation for configuring the implantable neuromodulation system. Stimulation parameters for stimulating the diaphragm may be titrated to determine if effective stimulation can be tolerated by the patient and overcome central apnea symptoms of the patient. Additional sensors may be used to detect the presence of obstructive apnea symptoms underlying treated central apneas. One or more respiratory inductance plethysmography belts may be used to determine the presence of obstructive apnea symptoms. One or more oxygen sensors may be used to determine the presence of obstructive apnea symptoms. A polysomnogram system may be used to determine the presence of obstructive apnea symptoms.

BRIEF DESCRIPTION OF THE DRAWINGS

A better understanding of the features and advantages of the methods and apparatuses described herein will be obtained by reference to the following detailed description that sets forth illustrative embodiments, and the accompanying drawings of which:

FIG. 7A shows an exemplary stimulation regimen for treating CSA. FIG. 7B shows an exemplary diaphragm EMG indicating a CSA pattern treated with the stimulation regimen indicated in FIG. 7A.

FIG. 8A shows an exemplary stimulation regimen for treating OSA. FIG. 8B shows an exemplary diaphragm EMG indicating a OSA pattern treated with the stimulation regimen indicated in FIG. 8A.

FIG. 9A shows an exemplary stimulation regimen for treating CSA. FIG. 9B shows sensor output indicating the presence of OSA events during the CSA treatment. FIG. 9C shows a diaphragm EMG indicating a CSA pattern treated with the stimulation regimen indicated in FIG. 9A.

FIG. 10A shows an exemplary stimulation regimen for treating CSA. FIG. 10B shows an exemplary stimulation regimen for treating OSA events. FIG. 10C shows a diaphragm EMG indicating a CSA pattern treated with the stimulation regimen indicated in FIG. 10A.

DETAILED DESCRIPTION

Figure 1:
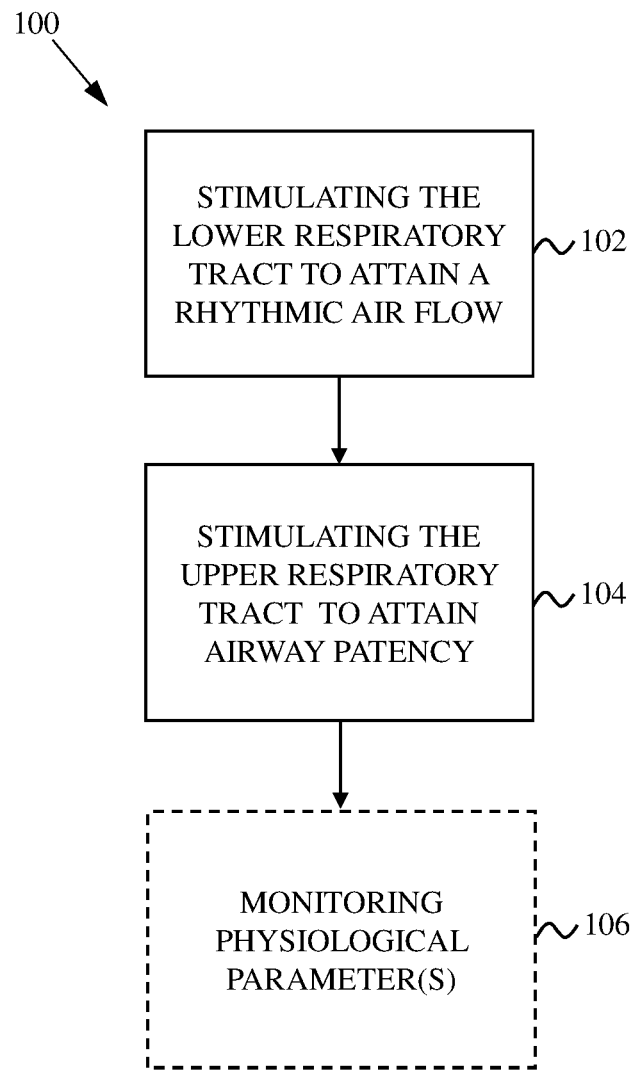
FIG. 1 shows a flowchart indicating a method for treating sleep apnea.

Methods and devices described herein can be used to treat various types of sleep apnea and/or hypopnea. Sleep apnea is generally characterized by pauses in respiration of about ten seconds or more. Hypopnea is generally characterized by a reduction in ventilation by at least 50% during sleep that results in a decrease in arterial saturation of 4% or more due to partial airway obstruction. It is appreciated that devices and methods of treating sleep apnea described herein may also be used to treat hypopnea. Types of sleep apnea can include central sleep apnea/hypopnea (CSA), obstructive sleep apnea/hypopnea (OSA) and combinations of central and obstructive sleep apnea/hypopnea. OSA generally involves the upper respiratory tract (also referred to as the upper airway), which includes parts of the mouth, nasal cavity, tongue, and other tissues above the sternal thorax. In OSA, tissues of the upper airway collapse into the airway passage when the patient relaxes during sleep, causing momentary blockages of air flow referred to as obstructed breathing. CSA generally involves the central control of respiration which control diaphragm contraction. In CSA, the brain's respiratory control centers may be imbalanced during sleep such that the sleeper misses one or more cycles of breathing, causing irregular breathing patterns such as Cheyne-Stokes respiration. Mixed sleep apnea can involve aspects of both obstructive and CSA, and therefore can involve both the upper and lower respiratory tracts.

Methods described herein may be used to treat obstructive sleep apnea by causing one or more muscles of the upper respiratory tract to contract, thereby at least partially moving collapsed tissue out of the upper airway and allowing the patient to breath normally during sleep. Methods described herein may be used to treat CSA by causing one or more muscles of the lower respiratory tract to rhythmically contract, thereby restoring normal rhythmic air flow (breathing) into the lungs during sleep. Methods described herein may be used to treat mixed sleep apnea by causing muscles of the upper and lower respiratory tracts to contract to attain upper airway patency and rhythmic air flow. The contractions can be coordinated such that proper breathing patterns can be maintained. The muscles contractions can be achieved by stimulating one or more nerves and/or one or more muscles of the upper and/or lower respiratory tract. In some cases, the stimulation involves using one or more electrodes to electrically stimulate the nerve and/or muscle. In some cases, the electrodes are implanted within the patient. Some of the systems and methods described herein can include those described in U.S. Pat. No. 7,840,270, filed Jul. 23, 2004, and titled "SYSTEM AND METHOD FOR CONDITIONING A DIAPHRAGM OF A PATIENT;" U.S. Pat. No. 7,962,215, filed Mar. 9, 2007, and titled "VENTILATORY ASSIST SYSTEM AND METHODS TO IMPROVE RESPIRATORY FUNCTION;" U.S. Pat. No. 8,478,412, filed Oct. 30, 2008, and titled "METHOD OF IMPROVING SLEEP DISORDERED BREATHING;" and U.S. Patent Application Publication No. 2018/0036033 A1, filed Aug. 3, 2017, and titled "SYSTEMS AND METHODS FOR ELECTRODE PLACEMENT IN DEEP MUSCLES AND NERVES USING ULTRASOUND GUIDANCE," each of which is incorporated herein by reference in its entirety.

The methods and devices described herein can provide a number of advantages over other sleep apnea treatment methods and devices. In some embodiments, the devices are configured to treat central, obstructive and complex apneas. The methods may be tested first using a trial system to assess effectiveness and tolerability for treating the sleep apnea. In some embodiments, the devices are modularized so that they provide flexibility and scalability for treating chronic sleep apneas.

Methods for Implementing Stimulation Regimens

Figure 2:
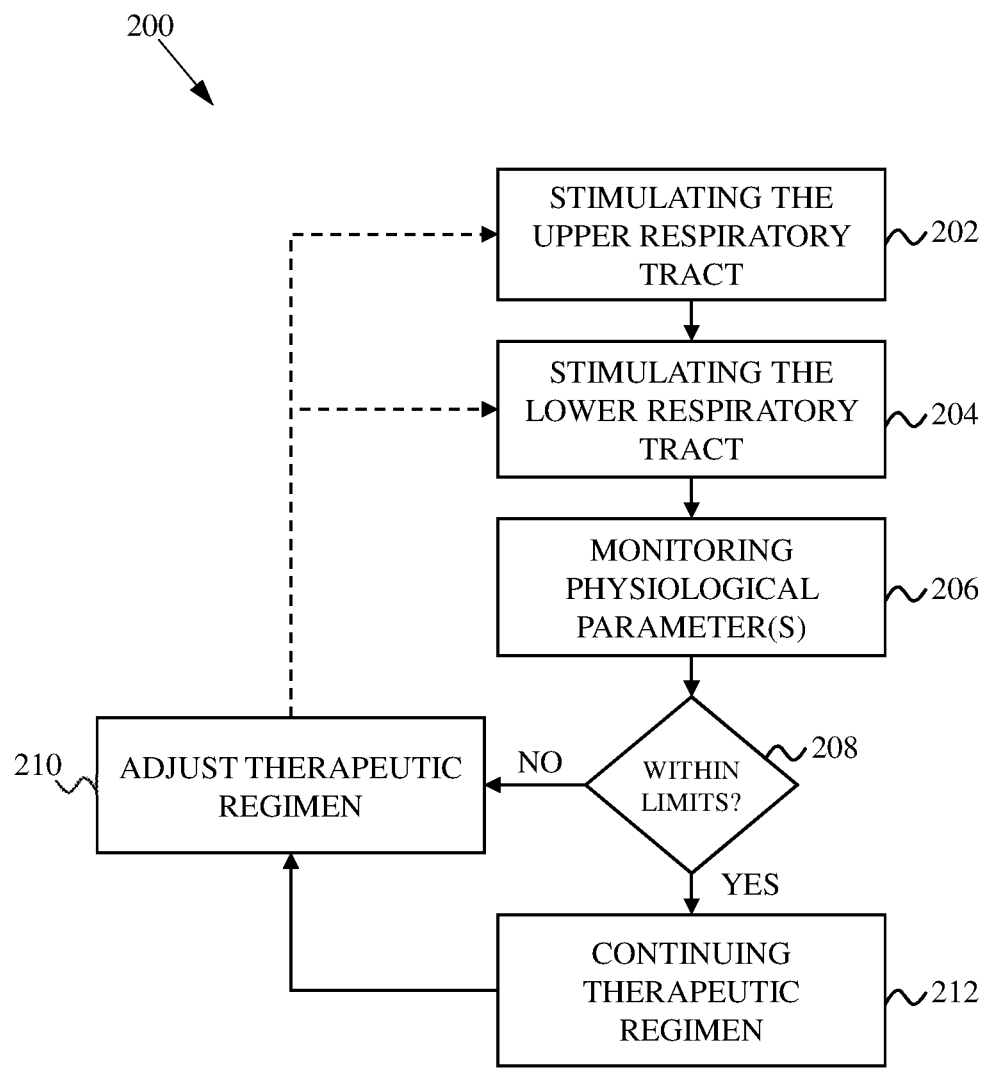
FIG. 2 shows a flowchart indicating another method for treating sleep apnea.
Figure 3:
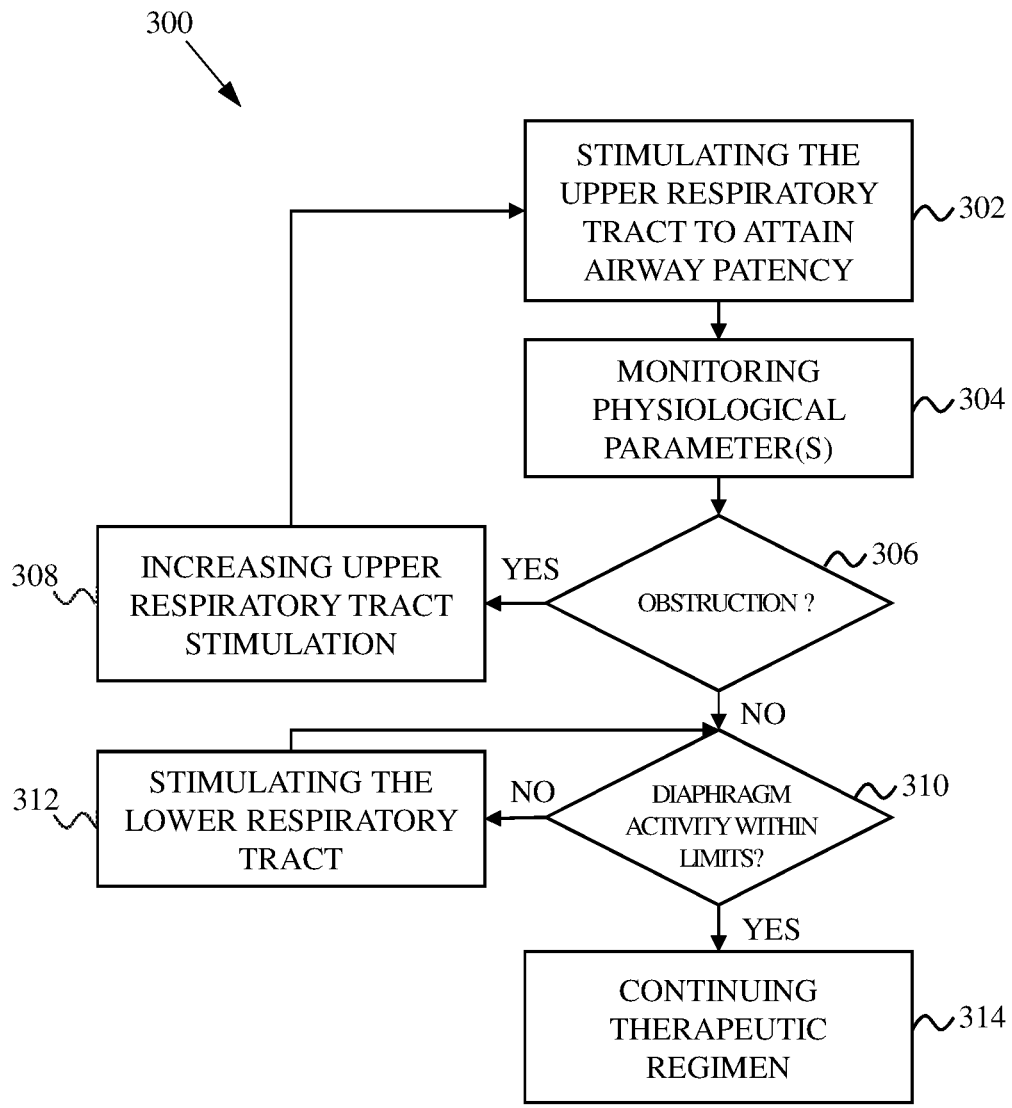
FIG. 3 shows a flowchart indicating another method for treating sleep apnea.

Methods described herein can involve stimulating the upper and/or lower respiratory tract in accordance with a stimulation regimen, which corresponds to a prescribed sequence of stimulations over a period of time, such as over a single sleep period (e.g., overnight) or over multiple sleep periods. The flowcharts of FIGS. 1-3 illustrate how stimulation regimen may be implemented in an open-loop mode, an closed-loop mode, or a combination mode whereby the stimulation regimen can be implemented in open-loop and/or closed-loop modes.

FIG. 1 shows a flowchart 100 indicating a method for treating sleep apnea according to an open-loop mode. At 102, the lower respiratory tract is stimulated to attain rhythmic air flow. In some cases, this involves stimulating a phrenic nerve, which is a nerve that originates in the neck and passes down between the lung and heart and to the diaphragm. There are two phrenic nerves—left and right. Stimulating one or both phrenic nerves can cause the diaphragm to contract and cause air to be drawn into the lungs (inspiration). The phrenic nerve(s) may be electrically stimulated using an electrode implanted into the patient's body, such as a nerve cuff electrode. In some cases, the electrode(s) are placed on phrenic nerve trunk. Repeated and rhythmic stimulation of the phrenic nerve(s) causes the diaphragm to rhythmically contract accordingly. Thus, a pattern of electrical pulses can be implemented to control the patient's breathing in accordance with normal sleep breathing patterns. In some cases, the diaphragm is stimulated directly using, for example, one or more electrodes implanted in the diaphragm. In some embodiments, the electrode(s) is/are placed in an inferior and/or a superior aspect location of the diaphragm. In some instances, one or more of the phrenic nerves and the diaphragm are stimulated.

At 104, the upper respiratory tract is stimulated to attain airway patency. In some cases, this involves stimulating the hypoglossal nerve, which is a nerve that passes through the neck to the tongue muscles. Stimulating the hypoglossal nerve can cause the tongue to move slightly forward in the mouth and open the airway. In some cases, airway patency is achieved by stimulating the recurrent laryngeal nerve, which is part of the vagus nerve and supplies intrinsic muscles of the larynx. Stimulating the recurrent laryngeal nerve can cause contraction of muscles of the larynx so that tissues of and around the larynx move away from the airway and allow air flow to pass. In some instances, both the hypoglossal nerve and the recurrent laryngeal nerve are stimulated. In some cases, the upper respiratory tract is stimulated with a continuous electric current. In other cases, the upper respiratory tract is stimulated with every breath of the patient.

The operations 102 and 104 can be each be implemented in accordance with a stimulation regimen, which corresponds to a prescribed sequence of stimulations over a period of time, such as over a single sleep period (e.g., overnight). The stimulation regimen may vary depending on the type and severity of an individual's sleep apnea, as well as whether characteristics of the sleep apnea change over time (e.g., over a single or multiple sleep periods). In some embodiments, the stimulation regimen for the upper respiratory tract involves stimulation for extended periods to keep the upper airway patent or just during sensed/predicted times of inspiration. Based on sensed respiratory rate, the upper airway stimulation could be turned on prior to the anticipated next inspiration and then turned off upon completion of the sensed inspiration activity.

The operations 102 and 104 may be implemented in an open-loop mode to maintain laminar airflow and protect against airway collapse by maintaining a respiratory rhythm. The operations 102 and 104 can be implemented in any sequence and can overlap over a sleep cycle. In one example, a mild electric stimulation is applied to the upper respiratory tract to attain an open upper airway, followed by a sequence of electric stimulations applied to the lower respiratory tract to create a rhythmic air flow while the upper respiratory tract continues to be stimulated to maintain the open airway. In another example, a rhythmic air flow is established by stimulating the lower respiratory tract, followed by opening the upper airway by stimulating the upper respiratory tract while the lower respiratory tract is being stimulated. In a further example, the upper respiratory tract is stimulated prophylactically to prevent obstructions, then the lower respiratory tract is stimulated to cause inspiration and to trigger the patent's respiratory generator. The lower respiratory tract simulation may be discontinued once the patient's respiratory generator establishes sufficient rhythmic breathing. In some cases, diaphragm contraction may create or exacerbate obstructions in the upper airway by creating a greater negative pressure in the upper airway. Thus, in some cases the stimulation regimen includes stimulating or increasing stimulus intensity (e.g., electric current) of the upper respiratory tract during diaphragm contraction. That is, a phrenic nerve and/or the diaphragm can be stimulated to create a series of inspirations, and the upper respiratory tract can be stimulated (or the simulation intensity can be increased) with every inspiration to compensate for the increased negative pressure. In other cases, the stimulus intensity of the upper respiratory tract is decreased during certain periods while the lower respiratory tract is stimulated. In some cases, diaphragm contraction may protect against airway collapse by maintaining a respiratory rhythm. Thus, in some case the stimulus intensity of the upper respiratory tract is maintained or decreased while the lower respiratory tract is stimulated.

At 106, one or more physiological parameters is optionally monitored, for example, to determine whether normal sleep pattern is attained and/or maintained over a period of time. The physiological parameters may include respiration rate, blood oxygen levels (e.g., pulse oximetry data), diaphragm activity or other muscle activity (e.g., EMG data) and/or other physiological parameters that can indicate normal sleep patterns. Respiration can be monitored, for example, using respiratory inductance plethysmography (RIP), which involves evaluating pulmonary ventilation by measuring the movement of the chest and abdominal wall. Heart activity may be monitored, for example, using electrocardiography (ECG or EKG). Brain activity may be monitored, for example, using electroencephalography (EEG). Eye activity may be monitored, for example, using electrooculography (EOG). In some cases, a polysomnogram (PSG) system is used, which may include sensors for monitoring brain activity (e.g., using EEG), eye movements (e.g., using EOG), muscle activity or skeletal muscle activation (e.g., using EMG), and heart rhythm (e.g., using ECG). Examples of RIP devices can include belts with sensors and that wrap around the patient's thorax and abdomen. Other ways of monitoring respiration can include the use of air flow sensors that measure the airflow within, for example, the upper airway (e.g., nose, mouth and/or throat). Diaphragm activity may be monitored using, for example, diaphragm electromyography (EMG) techniques, which involves recording electrical activity of the diaphragm on a temporal basis. Blood oxygen levels may be monitored using, for example, pulse oximetry techniques where oxygen desaturation levels in the blood are measured. A number of pulse oximetry devices are able to measure oxygen saturation non-invasively, such as through the skin (e.g., finger, wrist, earlobe, etc.). Low levels of blood oxygen may be an indication of inadequate respiration and oxygen supply to the blood. In some cases, the collected physiological parameter(s) data is analyzed to determine whether the stimulation regimen of 102 and/or 104 should be adjusted. In one example, the physiological parameter(s) is monitored to supplement an open-loop rhythm stimulation to the lower respiratory tract and to overcome a worsening obstruction.

Figure 6A:
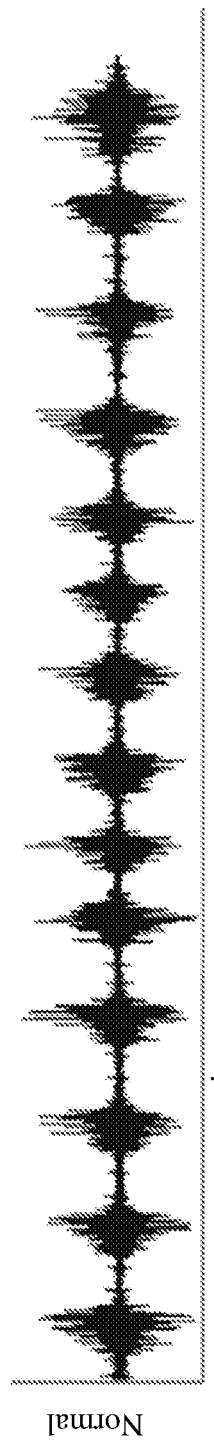
FIG. 6A shows an exemplary diaphragm EMG of a normal respiration pattern.
Figure 6C:
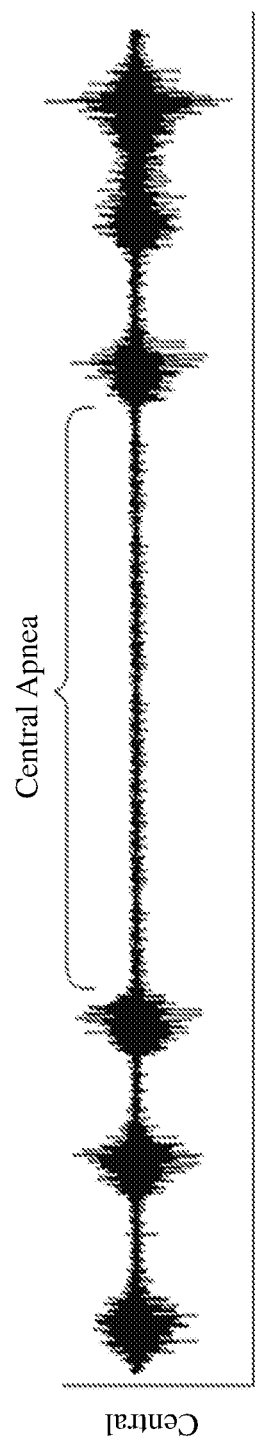
FIG. 6C shows an exemplary diaphragm EMG of an OSA respiration pattern.
Figure 6B:
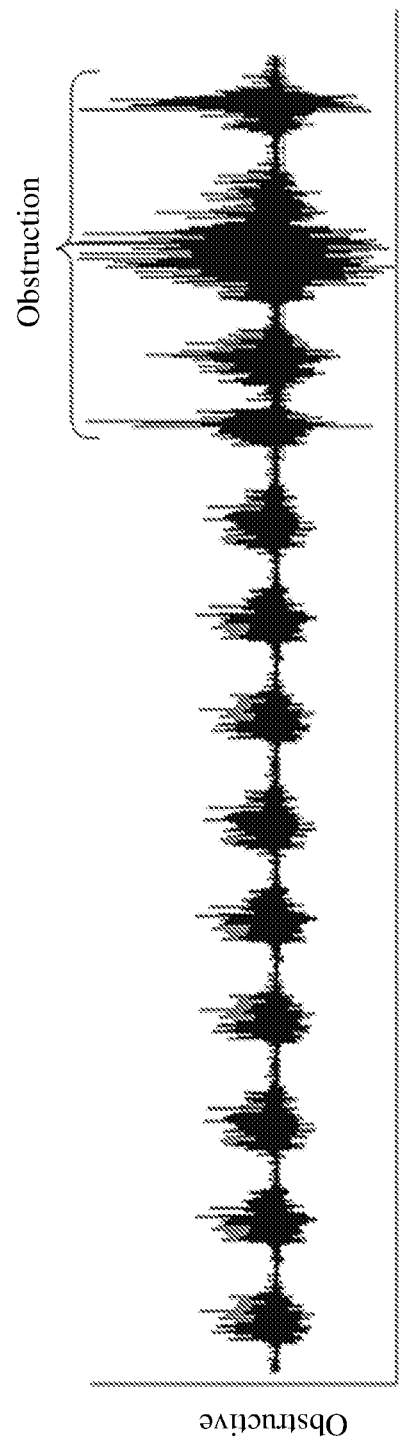
FIG. 6B shows an exemplary diaphragm EMG of a CSA respiration pattern.

In some embodiments, the stimulation regimen is implemented in a closed-loop, where one or more physiological parameters is monitored and used to adjust the therapeutic stimulation regimen in real time. In some cases, the stimulation regimen is implemented in an open-loop mode and optionally in a closed-loop mode, or in a closed-loop mode and optionally in an open-loop mode (i.e., combination modes). FIG. 2 shows a flowchart 200 indicating a method for treating sleep apnea using closed-loop or combination mode control. At 202, the upper respiratory tract (e.g., hypoglossal nerve and/or recurrent laryngeal nerve) is/are stimulated to clear the upper airway. At 204 the lower respiratory tract (e.g., phrenic nerve and/or diaphragm) is periodically stimulated to establish a rhythmic airflow to and from the lungs. The stimulation in 202 and 204 may be coordinated such that the upper airway is sufficiently clear during stimulation periods of the lower respiratory tract. At 206, at least one physiological parameter is monitored (e.g., in real time). At 208, the monitored data is used to determine whether the stimulation regimen of 202 and 204 is sufficiently maintaining uninterrupted and rhythmic airflow. This can involve determining whether the physiological parameter(s) is/are within acceptable limits, e.g., at or below an upper threshold and/or at or above a lower threshold. The thresholds will depend on the physiological parameter being monitored. For instance, a blood oxygen level below a predetermined threshold value (e.g., 95%, 90%, 85%, 80%, 75%, 70%, 65% or 60%) may be considered outside acceptable limits. For respiration and diaphragm activity, the thresholds may be associated with irregular patterns observed over a monitored period. To illustrate, FIGS. 6A-6C show exemplary diaphragm EMGs. FIG. 6A shows an exemplary diaphragm EMG of a normal respiration pattern, which may be characterized by regular periods of diaphragm activity separated by periods of diaphragm inactivity. FIG. 6B shows an exemplary diaphragm EMG of a CSA respiration pattern, which may be characterized by one or more time periods of diaphragm inactivity or under-activity (e.g., indicated "Central Apnea") that is/are longer than a predetermined time period (e.g., greater than about 10 seconds). The period of diaphragm inactivity can correspond to a pause of respiration due to imbalances in the brain's respiratory control centers. FIG. 6C shows an exemplary diaphragm EMG of an OSA respiration pattern, which may be characterized by one or more time periods of diaphragm over-activity (e.g., indicated "Obstruction") that is/are longer than a predetermined time period (e.g., greater than about 10 seconds). The period of diaphragm over-activity can correspond to a pause of respiration due to an obstruction of the upper airway.

If the diaphragm activity is within acceptable limits, at 212 the stimulation regimen of 202 and 204 can be continued. If the diaphragm activity is not within acceptable limits, at 210 the stimulation regimen can be adjusted to modify the stimulation of the upper respiratory tract 202 and/or the stimulation of the lower respiratory tract 204. The adjusted stimulation regimen can be continued until the diaphragm activity is determined to fall out of the established limits, in which case the stimulation regimen may be further adjusted. The monitoring and adjusting can be continued to maintain normal respiration through a patient's sleep period (e.g., overnight). This type of closed-loop treatment regimen may be well suited for treating complex type sleep apnea since the monitoring and adjusting may be done (e.g., substantially) in real time.

According to some embodiments, the upper respiratory tract may be adjusted based on the monitoring of diaphragm activity, and the lower respiratory tract may be optionally stimulated on an as-needed basis. FIG. 3 shows a flowchart 300 indicating a method of treating sleep apnea with an optional lower respiratory tract stimulation, which may be implemented in a closed-loop or combination mode. At 302, the upper respiratory tract (e.g., hypoglossal or recurrent laryngeal nerve) is stimulated according to a therapeutic stimulation regimen to attain airway patency. At 304, physiological parameter(s) is/are monitored. The physiological parameter(s) may include data associated with respiration (e.g., RIP data and/or air flow sensor data), blood oxygen levels (e.g., pulse oximetry data) and/or diaphragm activity (e.g., EMG data). The respiration and/or blood oxygen levels may be used to determine whether the upper respiratory tract is obstructed (i.e., OSA). The respiration, blood oxygen levels and/or diaphragm activity may be used to determine whether the diaphragm has irregular contractions (i.e., CSA). At 306, if the physiological parameter(s) indicates obstructed respiration (OSA), the stimulation to upper respiratory tract can be increased 308. This can cause the muscles of the upper tract (e.g., tongue and/or muscles of the larynx) to contract more and further open up the airway. In this way, the stimulation regimen for the upper tract can be adjusted in a closed-loop arrangement (e.g., in real time). At 310, if the physiological parameter(s) indicates irregular diaphragm contractions (CSA), the lower respiratory tract (e.g., diaphragm) can be stimulated 312 according to a corresponding stimulation regimen. The lower respiratory tract stimulating may also be adjusted in a closed-loop arrangement (e.g., in real time). Once the physiological parameter(s) indicates that the stimulation regimen(s) adequately provide normal sleep patterns, stimulation regimen is continued on the upper and/or lower respiratory tracts 314. In one example, electrodes implanted in the diaphragm sense: normal EMG activity levels and provide no stimulation, absence of EMG activity and stimulate the diaphragm to overcome central apnea, increased EMG activity and stimulate the upper airway nerves to overcome obstructive apnea, and absence of EMG activity and stimulate both the diaphragm and the upper airway to overcome complex apnea.

FIG. 7A shows a graph of an exemplary diaphragm stimulation regimen (e.g., voltage or current intensity over time) used to treat CSA as indicated by the diaphragm EMG shown in FIG. 7B. As described above, CSA may be characterized by diaphragm inactivity or under-activity. The CSA treatment regimen (FIG. 7A) can be implemented if diaphragm inactivity or under-activity is detected as being below a lower threshold (FIG. 7B, "CSA threshold"). The detection may be conducted over an evaluation period where the diaphragm signal time and/or amplitude are detected (indicated as "CSA, time and amplitude threshold detected"), which can occur over a predetermined period (e.g., between about 5 to about 10 seconds). After the diaphragm inactivity or under-activity is detected, the CSA stimulation regimen, which can include one or more pulses of electrical stimulation, can be applied to the lower respiratory system (e.g., diaphragm). The diaphragm activity can continue to be monitored during the CSA stimulation regimen is being applied. Once the diaphragm activity is detected as returning to or above the lower threshold, the stimulation regimen can be stopped. The diaphragm activity can continue to be monitored after the CSA stimulation regimen is applied to determine whether the diaphragm activity falls again below the lower threshold. If the diaphragm activity does fall below the lower threshold, the CSA stimulation regimen may be implemented again.

FIG. 8A shows a graph of an exemplary upper airway stimulation regimen (e.g., voltage or current intensity over time) used to treat OSA as indicated by the diaphragm EMG shown in FIG. 8B. As described above, OSA may be characterized by diaphragm over-activity. The OSA treatment regimen (FIG. 8A) can be implemented if diaphragm in over-activity is detected as being above an upper threshold (FIG. 8B, "OSA threshold"). The OSA stimulation regimen may include implementing one or more pulses of electrical stimulation to the upper respiratory system (e.g., hypoglossal and/or recurrent laryngeal nerve). The stimulation regimen can be provided until diaphragm EMG activity falls below the upper threshold or for a set inspiration duration. Once a normal level diaphragm activity is sensed again, the upper airway stimulation may be stopped. The OSA stimulation regimen may be implemented again if the diaphragm EMG is found to rise above the upper threshold again.

A complex apnea/hypopnea may occur due to an obstruction underlying a central apnea/hypopnea. In these cases, if a CSA event is treated with a stimulation regimen, the obstruction may become evident. If the CSA is masking the obstruction, the diaphragm EMG may not reveal the obstruction. The obstruction may be sensed using other techniques, such as RIP, air flow sensors and/or oxygen saturation techniques described herein. If the obstruction is determined to be consistently present with CSA, the obstruction can be anticipated and an upper airway treatment regimen can be turned on coincidental (or in advance) of the lower airway (e.g., diaphragm) stimulation. If the obstruction is determined not to always be present, the treatment may include 1) allowing the user to manually enable upper airway stimulation with lower airway (e.g., diaphragm) stimulation when needed, and/or 2) adding one or more additional sensors (external or implanted biosensor) to detect the obstruction and provide upper airway stimulation as needed. FIGS. 9A-9C show exemplary graphs indicating how a CSA treatment regimen can reveal an obstruction. FIG. 9A shows a diaphragm stimulation regimen (e.g., voltage or current intensity over time) for treating CSA as indicated by the diaphragm EMG shown in FIG. 9C. FIG. 9B shows sensor output (e.g., signal vs. time) for a RIP sensor used to monitor the movement of the chest and/or abdominal wall during the CSA treatment. The RIP sensor detects one or more OSA events subsequent to the CSA treatment. For example, the RIP sensor may detect one or more OSA events (e.g., FIG. 9B, "Event 1" and "Event 2") indicating chest and/or abdominal wall movement right after (out of sync with respect to) the initiation of one or more corresponding stimulation pulses (e.g., FIG. 9A, "Pulse 1" and "Pulse 2"). Note that other techniques may also be used to detect the OSA events, such as using an air flow sensor to detect events of lack of air flow through the nasal passageway. In cases where a percutaneous trial system is used, external sensors can be used to determine presence or consistence of OSA events.

Once OSA events have been determined to occur during CSA treatment and that the patient has a complex sleep apnea, a treatment regimen for addressing the OSA events can be implemented. FIGS. 10A-10C show exemplary graphs indicating a treatment regimen for a treating the OSA events revealed in FIGS. 9A-9C. FIG. 10A shows a diaphragm stimulation regimen for treating CSA as indicated by the diaphragm EMG shown in FIG. 10C. FIG. 10B an upper respiratory stimulation regimen for treating anticipated OSC events based on the RIP data of FIG. 9B. The respiratory stimulation regimen can include one or more pulses of electrical stimulation that temporally correspond to the anticipated OSC events.

Figure 11:
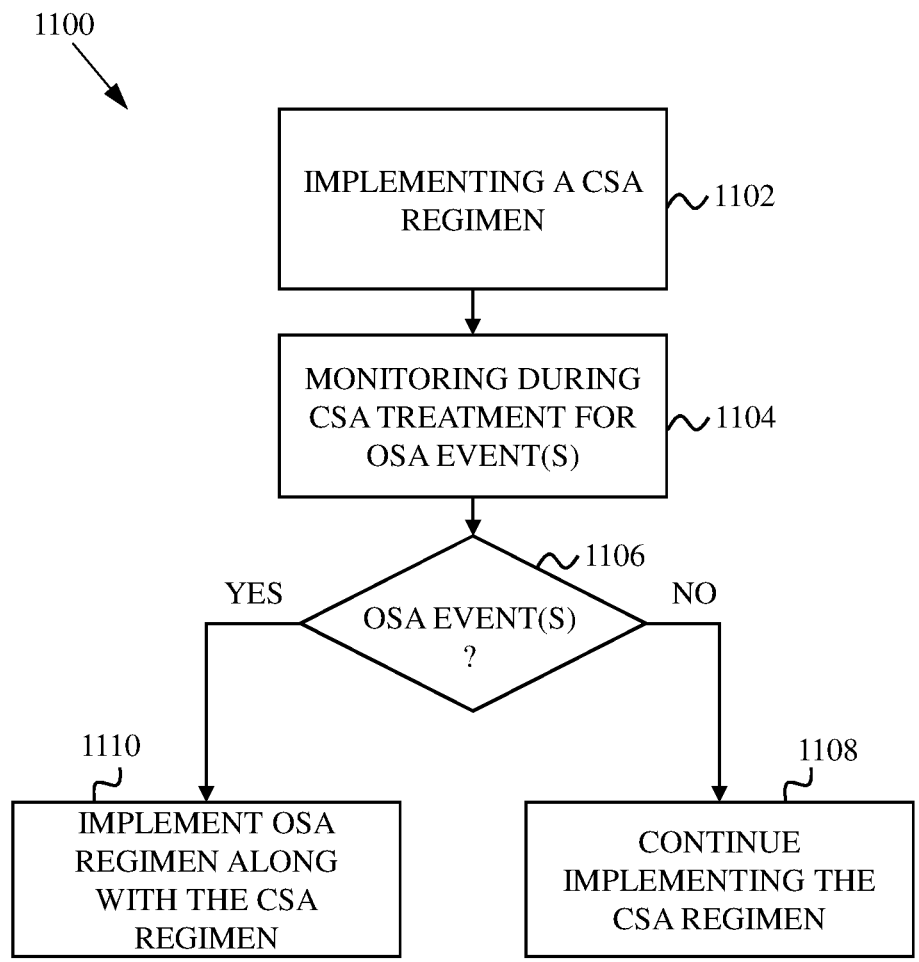
FIG. 11 shows a flowchart indicating a method for determining and treating obstructive sleep apnea events during treatment of central sleep apnea.

FIG. 11 shows a flowchart 1100 indicating a method of implementing a CSA stimulation regimen and determining and treating OSA events. At 1102, the lower respiratory tract (e.g., diaphragm) is stimulated according to a CSA stimulation regimen to attain a regular breathing pattern. At 1104, breathing patterns and/or blood oxygenation is monitored during implementation of the CSA treatment. The breathing patterns and/or blood oxygenation can be monitored, for example, using RIP, air flow and/or pulse oximetry device(s). At 1106, if the breathing patterns and/or blood oxygenation does not indicate one or more OSA events, the CSA regimen can be continued 1108. If the breathing patterns and/or blood oxygenation does indicate one or more OSA events, an OSA regimen can be implemented along with the CSA regimen 1110. The OSA regimen can be used to reduce the occurrence or severity of the obstructive airflow events.

Systems for Implementing Stimulation Regimens

Exemplary systems, apparatuses and components for implementing the stimulation methods described herein may include aspects of the NeuRx DPS™ System (provided by Synapse Biomedical, Inc. of Oberlin, Ohio) and described in U.S. Pat. Nos. 7,840,270, 7,962,215 and 8,478,412 and U.S. Patent Application Publication No. 2018/0036033 A1, each of which is incorporated herein by reference in its entirety.

Figure 4:
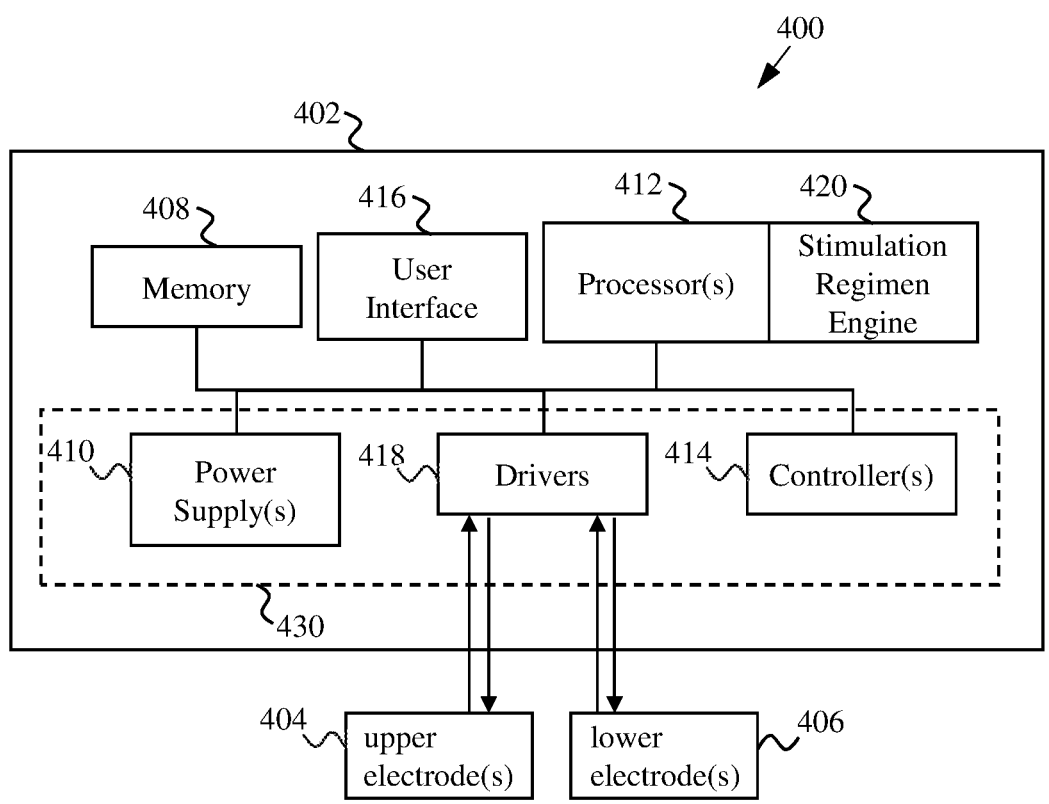
FIG. 4 shows a block diagram of a system for implementing methods described herein.

FIG. 4 shows a simplified block diagram of a system 400 according to some embodiments. The system 400 includes an electronic stimulator 402 that is configured to generate electronic signals to one or more electrodes for the upper respiratory system 404 (also referred to as upper electrodes) and/or one or more electrodes for the lower respiratory system 406 (also referred to as lower electrodes). As described herein, the upper electrode(s) 404 may be placed on nerves such as the hypoglossal nerve and/or the recurrent laryngeal nerve. The lower electrode(s) 406 may be placed on, for example, the phrenic nerve and/or on the diaphragm. In some embodiments, the electrodes are placed intramuscularly within the diaphragm (e.g., Permaloc™ or Transloc™ electrodes by Synapse Biomedical, Inc. of Oberlin, Ohio) in the inferior and/or superior aspect of the diaphragm. In some embodiments, the electrodes are alternatively or additionally placed on the phrenic trunks of the phrenic nerve. In some cases, the upper electrode(s) 404 and/or lower electrode(s) 406 are cuff electrodes, which may wrap at least partially around a nerve. The electrodes may be monopolar or bipolar electrodes. In some cases, the upper electrode(s) 404 and/or lower electrode(s) 406 are configured to stimulate (apply electric current) and sense (e.g., nerve or muscle activity). That is, a single electrode may be configured to stimulate and sense.

The electronic stimulator 402 can include one or more power supplies 410 configured to provide power for the various components of electronic stimulator 402, such as one or more processors 412 and one or more controllers 414 (e.g., microcontrollers). The processor(s) 412 can be configured to process data (e.g., EMG data) stored in memory 408 and generate a simulation regimen using a stimulation regimen engine 420. One or more controllers 414 can direct drivers 418 to send electronic signals in accordance with the stimulation regimen to the upper and/or lower electrodes 404 and/or 406. A user can control various functions of the electronic stimulator 402 via a user interface 416 (e.g., display). The processor(s) 412 may be configured to operate in an open-loop mode or a closed-loop mode. In a closed-loop mode, the processor(s) 412 may process and modify the stimulation regimen based on sensed data from the electrodes 404 and/or 406. For example, the stimulation regimen may be modified if sensed data associated with contraction of the diaphragm is at or above an obstruction threshold and/or at or below a diaphragm activity threshold, as described herein. In some instances, the electronic stimulator 402 allows the user to program a stimulation regimen using user interface 416. In some cases, the electronic stimulator 402 allows the user to select a custom stimulation regimen. In some embodiments, a least a portion of the electronic stimulator 402 is implanted into the patient's body. For example, an electronic stimulator portion 430 may part of an implantable unit that is implanted within a patient's body. The electronic stimulator portion 430 can be configured to communicate with a main control unit that is external to the body and includes the processor(s) 412. In some cases, the system 400 is configured to use information provided by one or more sensors other than electrodes 404 and 406 and that detect one or more physiological parameters (e.g., biosensors). The sensor(s) may be external to the body, such as RIP belts, nasal flow sensors and pulse oximetry sensor(s). The sensor(s) may be implanted within the body, such as implantable thoracic pressure sensor(s).

In some embodiments, the electrodes 404 and/or 406 is/are activated percutaneously (e.g., via one or more percutaneous connectors) with the electronic stimulator 402 being external to the body. A percutaneous set up may be well suited for applying a stimulation regimen on a trial basis, where the system 400 is used to sense and/or record a patient's diaphragm activity during sleep. A trial basis may be used to determination whether the patient has sleep apnea and/or whether the sleep apnea has characteristics of central, obstructive or mixed (e.g., complex) sleep apnea. The trial basis may also be used to determine whether open-loop stimulation of the lower airway (e.g., for laminar flow) would obviate the need for upper airway stimulation.

The electronic stimulator 402 can supply the lower electrode(s) 406 with electrical signal(s) that can be a capacitively-coupled, charge balanced, biphasic, constant current waveform with adjustable parameters as shown below in Table 1.

TABLE 1

| Parameter | Range |
| --- | --- |
| Onset Delay (from start) | 0-90 min |
| Stimulation On (inspiration) Time | 0.8-1.5 s |
| Respiratory Rate | 5-30 BPM |
| Burst Mode | On/Off |
| Output Pulse Period | 50-250 ms |
| Pulse Width Modulation Count | 0-10 |
| Cathodic Current Amplitude | 5-25 mA |
| Cathodic Current Pulse Width | 0-200 μs |

The electronic stimulator 402 can supply the upper electrode(s) 404 with electrical signal(s) that can be a capacitively-coupled, charge balanced, biphasic, constant current waveform with adjustable parameters as shown below in Table 2. It will be appreciated that the electrical signal of Table 1 and Table 2 can take the form of other waveforms for electrical stimulation such as monophasic or rectangular biphasic.

TABLE 2

| Parameter | Range |
| --- | --- |
| Onset Delay (from start) | 0-90 min |
| Continuous Stimulation | On/Off |
| Pre-inspiration On Time | 0-0.5 s |
| Stimulation On (inspiration) Time | 0.8-1.5 s |
| Respiratory Rate | 5-30 BPM |
| Output Pulse Period | 50-250 ms |
| Pulse Width Modulation Count | 0-10 |
| Cathodic Current Amplitude | 5-25 mA |
| Cathodic Current Pulse Width | 0-200 μs |

Figure 5:
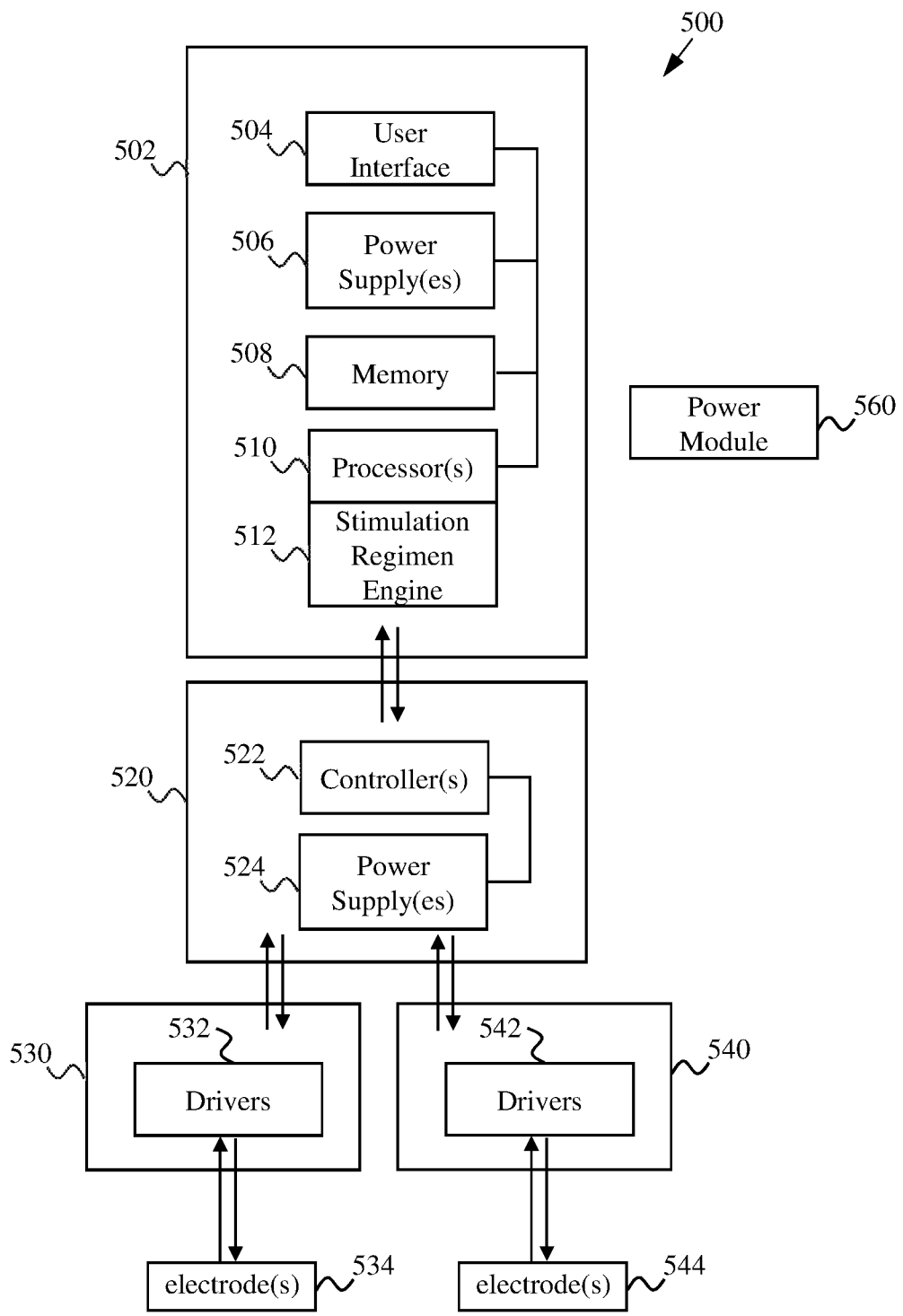
FIG. 5 shows a block diagram of modular system for implementing methods described herein.

According to some embodiments, the system includes modules that can operate in a network arrangement. FIG. 5 shows a simplified block diagram of modular system 500, which includes an external module 502, a primary implantable module 520, a first secondary implantable module 530 with associated one or more electrodes 534, and a second secondary implantable module 540 associated one or more electrodes 544. The implantable modules 520, 530 and 540 may be implanted within the body an in communication with each other, thus forming a network of modules within the body. The system 500 may include any of a number of primary and/or secondary implantable modules 520, 530 and 540 (e.g., one, two, three, four, etc.) The electrodes 534 and 544 may be place on a nerve or muscle, include stimulating and/or sensing electrodes, and/or include monopolar or bipolar electrode, as described herein.

The external module 502 includes a processor(s) 510 that processes data (e.g., EMG data) stored in memory 508 and generates a simulation regimen using a stimulation regimen engine 512. The stimulation regimen can be sent to the primary implantable module 520, which includes one or more controllers 522 that is/are operationally coupled with one or more power supplies 524 (e.g., one or more batteries). The primary implantable module 520 can be in communication with one or both of the secondary implantable modules 530 and 540. The primary implantable module 520 can direct one or both of the drivers 532 and 542 to provide electronic signals to one or both of the associated electrodes 534 and 544 in accordance with the stimulation regimen. In some cases, the primary implantable module 520 is additionally or alternatively configured to relay sensed data from electrode(s) 534 and/or 544 to the external module 502. The external module 502 may use the sensed data to modify the stimulation regimen (i.e., closed-loop or combination mode), as described herein. In some instances, the system 500 is configured to use information provided by one or more sensors other than electrodes 534 and 544 and that detect one or more physiological parameters (e.g., biosensors). The sensor(s) may be external to the body, such as RIP belts, nasal flow sensors and pulse oximetry sensor(s). The sensor(s) may be implanted within the body, such as implantable thoracic pressure sensor(s).

The external module 502 can be used to control various functions of implantable modules 520, 530 and 540. For example, the external module 502 can be used to turn the primary implantable module 520 on or off, thereby disconnecting power to the secondary implantable modules 530 and/or 540. As another example, the external module 502 can be used to charge the power supply(s) 524 (e.g., battery(s)) of the primary implantable module 520, which supplies power to the secondary implantable modules 530 and/or 540. The user may use a user interface 504 (e.g., display) of the external module 502 to control various aspects of the stimulation regimen implemented by the implantable modules 520, 530 and 540. For example, the user may use the external module 502 to select whether the system 500 operates in an open-loop mode or closed-loop mode. In some cases, the external module 502 allows the user to select a custom stimulation regimen (e.g., override a predetermined or calculated stimulation regimen). Thus, the external module 502 may act as a primary communication and power distribution module for the implantable modules 520, 530 and 540.

In some embodiments, the external module 502 communicates with the primary implantable module 520 using one or more wire connections, for example, via a percutaneous connector. In some embodiments, the external module 502 communicates with the primary implantable module 520 using a wireless communication, such as radio frequency communication and/or inductive charging. In wireless embodiments, the external module 502 may wirelessly communicate with the primary implantable module 520 implanted within the body through body tissues (e.g., skin). The primary implantable module 520 may communicate with one or both of the secondary implantable modules 530 and 540 via wire connections, which can allow for information and power transfer (e.g., power transfer from the primary implantable module 530 to one or both of the secondary implantable modules 530 and 540). In some cases, the secondary implantable modules 530 and 540 are implanted near the target stimulation or sensing site. For instance, the secondary implantable module 530 may be implanted proximal to the upper respiratory tract and the secondary implantable module 540 may be implanted proximal to the lower respiratory tract. In some embodiments, the primary implantable module 520 is implanted near one or both of the secondary implantable modules 530 and 540. In some embodiments, a separate power module 560 is used to turn the primary implantable module 520 on and off, while the external module 502 provides a stimulation regimen to the primary implantable module 520 and/or collect sensed data from the primary implantable module 520. For instance, a user may use the power module 560 to turn on the primary implantable module 520 before going to sleep, then turn off the primary implantable module 520 when awake or otherwise unneeded. In some embodiments, the power module 560 is in the form of a wand.

The modularized configuration of the system 500 can allow for flexible implementation and customization of a stimulation regimen to a patient's particular needs. In one example, one of the secondary implantable modules 530 and 540 acts as a stimulating module for applying stimulation to the diaphragm and/or the phrenic nerve, while the other one of the secondary implantable modules 530 and 540 acts as a sensing module for sensing nerve activity of the upper respiratory tract. In another example, one of the secondary implantable modules 530 and 540 acts as a stimulating module for applying stimulation to the upper respiratory tract, while the other one of the secondary implantable modules 530 and 540 acts as a stimulating module for stimulating the diaphragm and/or the phrenic nerve. In a further example, one of the secondary implantable modules 530 and 540 acts a stimulating and sensing module for the upper respiratory tract, while the other one of the secondary implantable modules 530 and 540 acts as a stimulating and sensing module for the lower respiratory tract. These examples are presented to illustrate that the implantable modules 520, 530 and 540 can be combined in any of a number of ways. In this way, the system 500 can be customized to stimulate and/or sense the upper and/or lower respiratory tracts based on, for example, whether the patient has CSA (e.g., exhibits Cheyne Stokes respiration), OSA or mixed sleep apnea. The modularized configuration of system 500 can also allow the external module 502 to be replaced or upgraded without having to remove the implantable modules 520, 530 and 540 from the body.

The modules of a modularized system can be customized to a patient's needs. For instance, in some cases, an upper airway stimulation module is implanted into the patient's upper airway. The upper airway module can be programmed to apply electrical stimulation only when an OSA event occurs based on input from a diaphragm EMG sensing module monitoring the patient's diaphragm. Alternatively, the upper airway module can be programmed to apply electrical stimulation with each CSA event. In some cases, the system is configured to allow the patient to choose when to apply the electrical stimulation. For instance, a lower airway module can be configured to apply a stimulation regimen to the diaphragm to treat CSA while an upper airway module can be configured to allow the patient to manually enable and disable OSA electrical stimulation in real time—for example, if the patient feels like sleep is being interrupted by OSA during the night or prophylactically before going to sleep. An obstruction sensor (e.g., RIP) can be used to trigger an upper airway module to stimulate with CSA events when an obstruction event is sensed. The modularized system may be flexible and scalable. For example, for treating CSA, the system can include only a diaphragm stimulating module (e.g., as low cost chronic percutaneous system). As another example, for treating CSA, a system can include an implanted diaphragm stimulating module that may be upgradable by implanting a diaphragm sensing module. As a further example, for treating OSA, a system can include an upper airway stimulating module and an implanted diaphragm sensing module. As an additional example, for treating CSA and OSA, the system can include an implanted diaphragm stimulating module and an implanted upper airway module, which are programmed for synchronous or manually-enabled stimulation for obstructive events. As another example, for treating CSA and OSA, the system can include an obstruction sensing module with one or more external or implanted physiological sensors.

Example 1

A patient is determined to exhibit CSA or OSA symptoms by monitoring the diaphragm activity (e.g., using a trial system). An electronic stimulator is implanted in the patient's body. If the patient has CSA, the electronic stimulator is implanted proximate to the lower respiratory tract. If the patient has OSA, the electronic stimulator is implanted proximate to the upper respiratory tract. The patient uses a main control unit to implement an open-loop stimulation regimen at night to stimulate the upper respiratory tract (for OSA) or lower respiratory tract (for CSA) in accordance with a stimulation regimen.

Example 2

A patient is determined to exhibit CSA symptoms by monitoring the diaphragm activity (e.g., using a trial system). A primary implantable module and a secondary implantable module (and associated electrode(s)) are implanted in the patient's body. The patient uses a main module to implement an open-loop or closed-loop stimulation regimen at night to stimulate the lower respiratory tract (e.g., contraction of the diaphragm) in accordance with a stimulation regimen a rhythmic airflow. If the patient develops OSA, another secondary implantable module (and associated electrode(s)) is implanted in the patient's body. The patient uses a main module to implement an open-loop or closed-loop stimulation regimen to the upper respiratory tract in addition to the lower respiratory tract.

Example 3

A patient is determined to exhibit CSA symptoms by monitoring the diaphragm activity (e.g., using a trial system). A primary implantable module and a secondary implantable module (and associated electrode(s)) are implanted in the patient's body. The patient uses a main module to implement a closed-loop stimulation regimen at night to stimulate the lower respiratory tract (e.g., contraction of the diaphragm) in accordance with a stimulation regimen. The primary implantable module relays diaphragm activity data to the main module, which is used by the main module to adjust the stimulation regimen while the patient is sleeping.

Example 4

A patient is determined to exhibit OSA symptoms by monitoring the diaphragm activity (e.g., using a trial system). A primary implantable module and two secondary implantable modules (and associated electrodes) are implanted in the patient's body. A first secondary implantable module is arranged to electrically stimulate the upper respiratory tract. A second secondary implantable module is arranged to sense diaphragm activity. The patient uses a main module to implement an open-loop stimulation regimen using the first secondary implantable module to stimulate the upper respiratory tract in accordance to clear the airway during sleep. The second secondary implantable module monitors diaphragm activity data, which is sent to and collected by the main module. The collected data is analyzed to determine how effective the stimulation regimen to the upper respiratory tract was for creating a patent airway. The stimulation regimen can be modified based on the collected data.

Example 5

A patient is determined to exhibit complex sleep apnea symptoms by monitoring the diaphragm activity (e.g., using a trial system). A primary implantable module and two secondary implantable modules (and associated electrodes) are implanted in the patient's body. A first secondary implantable module is arranged to electrically stimulate the upper respiratory tract. A second secondary implantable module is arranged to stimulate the lower respiratory tract. The patient uses a main module to implement a stimulation regimen using the first secondary implantable module to stimulate the upper respiratory tract and the second secondary implantable module to stimulate the lower respiratory tract.

Example 6

A patient is determined to exhibit CSA symptoms by monitoring the diaphragm activity using a trial system. The trial system is used to implement a trial stimulation regimen to the phrenic nerve for rhythmic contraction of the diaphragm. The patient experiences pain during implementation a trial stimulation regimen. The trial stimulation regimen is modified to include a burst mode, or the location of the electrode (e.g., nerve cuff) is moved to a different region of the phrenic nerve, to sufficiently mitigate the pain while still providing sufficient rhythmic contraction of the diaphragm. The burst mode of stimulation consists of a high frequency (nominally 1 KHz) sequence of stimulation pulses delivered at a lower stimulus amplitude. The charge per phase of the burst sequence may be equivalent or higher than the single, higher amplitude, pulse that elicited pain. Because of the lower amplitude of the individual pulses, within the burst, depolarization thresholds of pain fibers may not be reached and thus pain avoided. If an effective diaphragm contraction is achieved, that the patient is able to tolerate, an implanted system is implanted in the patient's body and the modified trial stimulation regimen is implemented, or the modified location of the electrode is used, to provide rhythmic airflow during sleep.

Example 7

A patient is determined to exhibit CSA symptoms by monitoring the diaphragm activity using a percutaneous trial system. The percutaneous trial system is used to implement a CSA treatment regimen and confirm that the treatment overcomes the CSA and the patient tolerates the stimulation without additional waking. One or more additional external sensing components (e.g., RIP belt(s), air flow sensor(s) and/or oxygen desaturation sensor(s)) are used to determine if there are additional OSA components underlying the treated CSA. An OSA treatment regimen to overcome the CSA and OSA prescribed. The patient uses the trial system with the external sensing component(s) to confirm that the CSA and OSA symptoms are overcome and that the patient is able to tolerate the patient prescribed stimulation regimen. An implanted system is implanted into the patient, and the CSA and OSA treatment regimens are used to treat the complex apnea.

Any of the methods (including user interfaces) described herein may be implemented as software, hardware or firmware, and may be described as a non-transitory computer-readable storage medium storing a set of instructions capable of being executed by a processor (e.g., computer, tablet, smartphone, etc.), that when executed by the processor causes the processor to control perform any of the steps, including but not limited to: displaying, communicating with the user, analyzing, modifying parameters (including timing, frequency, intensity, etc.), determining, alerting, or the like.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A method of treating sleep apnea, comprising:
   (a) repeatedly stimulating one or both of a phrenic nerve and a diaphragm, or increasing a stimulus intensity applied to one or both of the phrenic nerve and the diaphragm, in accordance with a rhythmic air flow when a diaphragm electromyographic (EMG) activity is below a first threshold; and
   (b) stimulating an upper respiratory nerve, or increasing a stimulus intensity applied to the upper respiratory nerve, to maintain an upper airway patency when the EMG activity is above a second threshold.

2. The method of claim 1, wherein the stimulating in (b) is varied based on a pattern of stimulations in (a).

3. The method of claim 2, wherein (b) comprises stimulating or increasing the stimulus intensity applied to the upper respiratory nerve during periods when one or both of the phrenic nerve and the diaphragm is stimulated.

4. The method of claim 1, wherein (b) comprises maintaining the stimulus intensity of the upper respiratory nerve during (a).

5. The method of claim 1, further comprising sensing the EMG activity using one or more electrodes placed at one or more locations of the diaphragm.

6. The method of claim 5, wherein the one or more locations comprises an intramuscular location of the diaphragm or on a phrenic nerve trunk.

7. The method of claim 5, wherein the one or more locations includes an inferior or a superior aspect location of the diaphragm.

8. The method of claim 1, wherein increasing the stimulus intensity comprises increasing an electrical current delivered to the upper respiratory nerve, the phrenic nerve or the diaphragm.

9. The method of claim 1, further comprising sensing pulmonary ventilation and/or blood oxygen levels.

10. The method of claim 1, further comprising stopping stimulation to one or more of the phrenic nerve and the diaphragm when the EMG activity is above the first threshold.

11. The method of claim 1, further comprising stopping stimulation to the upper respiratory nerve when the EMG activity is below the second threshold.

12. The method of claim 1, wherein the first threshold is a lower threshold, and wherein the second threshold is an upper threshold.

13. The method of claim 1, wherein at least a portion of the stimulating in (b) occurs during the repeated stimulating in (a).

14. The method of claim 1, wherein the first threshold is a central sleep apnea/hypopnea (CSA) threshold.

15. The method of claim 1, wherein the second threshold is an obstructive sleep apnea/hypopnea (OSA) threshold.

16. A system for treating sleep apnea, comprising:
   one or more controllers;
   one or more first electrodes operably coupled to the one or more controllers and configured to stimulate a phrenic nerve and a diaphragm of a patient;
   one or more second electrodes operably coupled to the one or more controllers and configured to stimulate an upper respiratory nerve of the patient;
   one or more sensing electrodes configured to sense a diaphragm electromyographic (EMG) activity of the diaphragm of the patient; and
   a processor configured to cause the one or more controllers, via the one or more first electrodes and the one or more second electrodes, to:
   (a) repeatedly stimulating one or both of the phrenic nerve and the diaphragm, or increasing a stimulus intensity applied to one or both of the phrenic nerve and the diaphragm, in accordance with a rhythmic air flow when the EMG activity is below a first threshold; and (b) stimulating the upper respiratory nerve, or increasing a stimulus intensity applied to the upper respiratory nerve, to maintain an upper airway patency when the EMG activity is above a second threshold.

17. The system of claim 16, further comprising a memory configured to store EMG activity data.

18. The system of claim 16, wherein the system comprises an implantable electronic stimulator portion that is configured to communicate with a main control unit that is external to the patient's body.

19. The system of claim 18, wherein the implantable electronic stimulator portion comprises the one or more controllers and one or more power supplies.

20. The system of claim 16, wherein (b) comprises stimulating or increasing the stimulus intensity applied to the upper respiratory nerve during periods when one or both of the phrenic nerve and the diaphragm is stimulated.

21. The system of claim 16, wherein (b) comprises maintaining the stimulus intensity of the upper respiratory nerve during (a).

22. The system of claim 16, wherein the first threshold is a central sleep apnea/hypopnea (CSA) threshold.

23. The system of claim 16, wherein the second threshold is an obstructive sleep apnea/hypopnea (OSA) threshold.

* * * * *